US012661231B2

(12) United States Patent
Little et al.

(10) Patent No.: US 12,661,231 B2
(45) Date of Patent: Jun. 23, 2026

(54) CONNECTION MECHANISMS FOR USE WITH ORTHOPEDIC INSTRUMENTS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Aaron N. Little, Cordova, TN (US); Jeffrey N. Yeager, Nesbit, MS (US); Tom J. Francis, Cordova, TN (US); Jason S. Jordan, Hernando, MS (US); Tedd Dixon, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 192 days.

(21) Appl. No.: 18/513,030

(22) Filed: Nov. 17, 2023

(65) Prior Publication Data

US 2024/0197487 A1 Jun. 20, 2024

Related U.S. Application Data

(60) Provisional application No. 63/432,793, filed on Dec. 15, 2022.

(51) Int. Cl.
| | |
|---|---|
| *A61F 2/38* | (2006.01) |
| *A61B 17/15* | (2006.01) |

(Continued)

(52) U.S. Cl.
CPC .......... *A61F 2/389* (2013.01); *A61B 17/1604* (2013.01); *A61B 17/1764* (2013.01);
(Continued)

(58) Field of Classification Search
CPC .......... A61F 2/46; A61F 2/4684; A61F 2/389; A61F 2/38; A61F 2/461; A61F 2/64;
(Continued)

(56) References Cited

U.S. PATENT DOCUMENTS

| | | | |
|---|---|---|---|
| 9,655,750 B2 | 5/2017 | Marter | |
| 11,304,826 B1 | 4/2022 | Cyko et al. | |

(Continued)

OTHER PUBLICATIONS

Attune Knee System: Intuition Instruments—© 2022 DePuy Synthes—Surgical Technique, 136 pages.

*Primary Examiner* — Marcela I. Shirsat
(74) *Attorney, Agent, or Firm* — KDW Firm PLLC

(57) ABSTRACT

Orthopedic systems, methods, and instrumentation for preforming knee arthroplasty. In some embodiments, the systems, methods, and instruments utilized improved quick connect mechanisms such as, for example, snap-fit connectors, to facilitate easier assembly and disassembly of the various components. For example, various connection mechanisms for coupling a tibial base trial to a guide (e.g., a fin punch guide), and/or for coupling the guide (e.g., fin punch guide) to a punch. In use, the systems, methods, and instruments provide an improved workflow for facilitating knee arthroplasty surgery.

6 Claims, 21 Drawing Sheets

(51) Int. Cl.

| | |
|---|---|
| *A61B 17/16* | (2006.01) |
| *A61B 17/17* | (2006.01) |
| *A61F 2/42* | (2006.01) |
| *A61F 2/46* | (2006.01) |

(52) U.S. Cl.
CPC .......... *A61F 2/4684* (2013.01); *A61B 17/154* (2013.01); *A61B 17/157* (2013.01); *A61B 17/1675* (2013.01); *A61B 17/1732* (2013.01); *A61B 17/1735* (2013.01); *A61B 17/1739* (2013.01); *A61F 2002/3895* (2013.01); *A61F 2002/4205* (2013.01); *A61F 2/461* (2013.01); *A61F 2220/0025* (2013.01)

(58) Field of Classification Search
CPC ...... A61F 2002/3895; A61F 2002/4205; A61F 2220/0025; A61B 17/16; A61B 17/17; A61B 17/1604; A61B 17/1764; A61B 17/1739; A61B 17/1732; A61B 17/1735; A61B 17/15; A61B 17/157; A61B 17/154; A61B 17/1675
USPC .......................................................... 606/88
See application file for complete search history.

(56) References Cited

U.S. PATENT DOCUMENTS

| | | | |
|---|---|---|---|
| 2005/0075640 A1* | 4/2005 | Collazo .............. | A61B 17/1764 606/86 R |
| 2007/0233117 A1* | 10/2007 | Butler ................... | A61F 2/4465 606/273 |
| 2013/0289570 A1* | 10/2013 | Chao ................... | A61B 17/1764 606/88 |
| 2023/0157831 A1* | 5/2023 | Harris, Jr. ............... | A61F 2/389 623/20.32 |

* cited by examiner

CONNECTION MECHANISMS FOR USE WITH ORTHOPEDIC INSTRUMENTS

CROSS-REFERENCE TO RELATED APPLICATIONS

This is a non-provisional of, and claims the benefit of the filing date of, U.S. provisional patent application No. 63/432,793, filed Dec. 15, 2022, entitled "Connection Mechanisms for Use with Orthopedic Instruments," the entirety of which application is incorporated by reference herein.

TECHNICAL FIELD

The present disclosure is directed to orthopedic instruments for preparing one or more patient's bones and more specifically to instrumentation systems for preparing a patient's knee for an implant.

BACKGROUND

Knee replacement surgery often entails removing the worn and damaged end portions of a person's distal femur and proximal tibia and replacing them with an orthopedic knee implant. In use, orthopedic knee implants replace the patient's damaged bone and/or articular cartilage and are intended to reduce pain and restore at least a measure of mobility to the patient. During the surgery, it is important for the surgeon to pick the proper implant size, location, and orientation for the implant on the femur and tibia. The surgeon should also properly balance the patient's ligaments so as to reduce pain, discomfort, and uneven distribution of forces in the knee.

Generally speaking, after the patient's distal femur and proximal tibia have been resected, the surgeon verifies that the proper amount of bone has been removed. This step is to ensure that the amount of bone removed is greater than the minimum thickness of implant offerings. The surgeon also ensures the presences of a consistent gap between the femoral implant and the tibia implant in both flexion and extension so that the medial and lateral collateral ligaments are properly tensioned throughout the range of motion. In order to determine the flexion and extension gaps, the surgeon typically places spacer blocks and accompanying shims onto a tibia base trial. Once the final thickness of the tibia implant has been verified, a tibia trial insert is inserted onto the tibia base trial and the knee is put through a range of motion. These shims, spacers, and trial inserts should securely mate or couple with each other and to the tibia base trial. They must also be disassembled after use. However, current designs of mating components typically use retaining rings, which are prone to falling out and functioning improperly. Other mating component designs include use a spring mechanism to provide friction to ensure components are not unintentionally disconnected.

These designs suffer from a number of disadvantages. For example, current designs do not provide feedback to the user to indicate that the shims, spacers, and/or trials have been properly connected. In addition, these designs are generally complex because they use springs and retaining rings. Furthermore, these designs are harder to clean and sterilize after a surgery due to the spaces inherent within these designs.

It would be beneficial to have a connection mechanism that provides audible and haptic feedback to a user indicating that the components have been properly connected. It would also be advantageous to have a connection mechanism with differing degrees of push in and pull-out forces to make assembly and disassembly easier.

It would also be beneficial to provide surgeons with instrumentation designed to minimize the number of distinct and separate steps performed in a knee replacement procedure. Reducing the number of distinct and separate steps, reduces operating room (OR) time, which has been shown to be beneficial to patients. Current orthopedic knee instrumentation does not optimize the surgical workflow. For example, during a typical knee replacement surgery, a surgeon may need to prepare an opening in a resected tibia to accept a tibia implant fin or keel. This step involves coupling a fin punch guide to a tibia base trial, selecting the proper size of tibia fin punch, attaching a fin punch to a handle, and guiding the fin punch through the fin punch guide and into the patient's tibia. After the opening in the tibia has been prepared, all the components (fin punch, fin punch guide, and tibia base trial) must be removed and disassembled before the implant may be installed. It would be advantageous to improve the overall efficiency of this process.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with one or more features of the present disclosure, in some embodiments, a method of performing knee arthroplasty surgery is disclosed. The method including placing a tibia base trial onto a resected tibia of a patient, coupling a fin punch guide to the tibia base trial via a first snap-fit connection between the tibia base trial and the fin punch guide. In addition, the fin punch guide includes a tab having an end portion for contacting a surface formed in a recess of the tibia base trial. The method further includes coupling a fin punch to the fin punch guide via a second snap-fit connection between the fin punch and the fin punch guide, at least a portion of the fin punch extending through a passageway formed in the fin punch guide and the tibia base trial and into the patient's resected tibia. The fin punch further includes a projection for contacting the tab associated with the fin punch guide to move the tab from a first position to a second position to release the surface formed in the recess. Finally, the method includes removing the fin punch and the fin punch guide from the tibia base trial.

In any preceding or subsequent example, the method further includes inserting one or more fixation pins through the tibia base trial and into the resected tibia to secure the tibia base trial to the resected tibia.

In any preceding or subsequent example, the first snap-fit connection includes at least one first connector associated with the tibial base trial and at least one second connector associated with the fin punch guide. At least one of the first connector and the second connector includes a male mating feature, and the other one of the first connector and the second connector includes a female mating feature.

In any preceding or subsequent example, the second snap-fit connection includes at least one third connector associated with the fin punch guide and at least one fourth connector associated with the fin punch. At least one of the third connector and the fourth connector includes a male mating feature, and the other one of the third connector and the fourth connector includes a female mating feature.

In any preceding or subsequent example, the male mating feature includes a boss and a plurality of tabs spaced circumferentially about the boss and the female mating feature includes a recess arranged and configured to receive the male mating feature.

In any preceding or subsequent example, the recess includes a circumferential chamfer arranged and configured to guide insertion of the male mating feature, a first section having a first diameter, and a second section having a second diameter, wherein the second diameter is greater than the first diameter.

In any preceding or subsequent example, coupling the male mating feature to the female mating feature provides tactical feedback including an audible sound.

In accordance with one or more features of the present disclosure, in some embodiments, an orthopedic knee system includes a tibial base trial, a fin punch guide, and a fin punch. The tibial base trial includes an inferior surface arranged and configured to contact a resected tibia, a superior surface opposite the inferior surface, and at least one first connector. The fin punch guide includes an inferior surface arranged and configured to contact the superior surface of the tibial base trial, a superior surface opposite the inferior surface, at least one second connector arranged and configured to couple with the at least one first connector, and at least one third connector. The fin punch includes at least one fourth connector arranged and configured to couple with the at least one third connector. At least one of the first connector and the second connector includes a male mating feature, and the other one of the first connector and the second connector includes a female mating feature. At least one of the third connector and the fourth connector includes a male mating feature, and the other one of the third connector and the fourth connector includes a female mating feature.

In any preceding or subsequent example, the male mating feature includes a boss and a plurality of tabs spaced circumferentially about the boss and the female mating feature includes a recess arranged and configured to receive the male mating feature.

In any preceding or subsequent example, the recess includes a circumferential chamfer arranged and configured to guide insertion of the male mating feature, a first section having a first diameter, and a second section having a second diameter, wherein the second diameter is greater than the first diameter.

In any preceding or subsequent example, coupling the male mating feature to the female mating feature provides tactical feedback including an audible sound.

In any preceding or subsequent example, the fin punch guide further includes a fin punch guide tab including a lever or hook-shaped end portion, and the tibial base trial includes a recess including a surface, the lever or hook-shaped end portion arranged and configured to reside within the recess and to contact the surface when the fin punch guide is coupled to the tibial base trial.

In any preceding or subsequent example, the fin punch further includes a projection or tab arranged and configured to contact the fin punch guide tab during connection of the fin punch to the fin punch guide, contact of the projection or tab moving the fin punch guide tab to a second position thereby releasing the lever or hook-shaped end portion from the recess so that removing the fin punch causes the fin punch guide to disconnect from the tibial base trial.

In any preceding or subsequent example, the tibial base trial includes a first passageway formed therein, the fin punch guide includes a second passageway formed therein, the second passageway aligned with the first passageway when the fin punch guide is coupled to the tibial base trial so that a portion of the fin punch can pass through the fin punch guide, through the tibial base trial and into the resected tibia.

In accordance with one or more features of the present disclosure, in some embodiments, a connection mechanism for releasably attaching a first component and a second component of an orthopedic apparatus is disclosed. In some embodiments, the connection mechanism includes a boss extending from a first surface of the first component, the boss including a first free end and a first side wall extending from the first free end to the first surface. The connection mechanism further includes a plurality of tabs extending around and spaced apart from the first side wall of the boss, each of the plurality of tabs having a second free end and a second side wall extending from the second free end to the first surface. In some embodiments, the second free end further includes, or is defined by, a projection extending in a direction away from the boss to an end portion.

The second component includes a recess extending into an interior thereof, the recess arranged and configured to receive the boss and the plurality of tabs when the first component is attached to the second component. In some embodiments, the recess includes, or is defined by, a circumferential chamfer where the recess meets a second surface of the second component. The recess further includes a first section with a first diameter adjacent the circumferential chamfer and extending into the recess, and a second section adjacent the first section and having a second, larger diameter. In use, each of the plurality of tabs is a resiliently flexible member and the projections are configured to engage with the second section to provide a snap-fit connection between the plurality of tabs and the second section.

In some embodiments, the first component may be a spacer and the second component may be a tibia trial insert. In other embodiments, the first component may be a fin punch guide and the second component may be a tibia base trial. Alternatively, the first component may be a fin punch and the second component may be a fin punch guide. The first component may also be a tibia base trial and the second component may be a tibia trial spacer or tibia trial insert.

In further embodiments, an audible sound is produced when the first component and the second component are connected. In an additional embodiment, the boss and the plurality of tabs are spaced apart to define a maximum deflection of the plurality of tabs. In an additional embodiment, the plurality of tabs are in a deformed condition or in an un-deformed condition when engaged with the second section. In yet another embodiment, the boss may be omitted.

In further embodiments, the projection may include a chamfer extending from an underside of the projection, the chamfer configured to control the force required to disconnect or decouple the first component and the second component. Additionally, the chamfer may be further defined by a first angle, the first angle having a first vertex at the end portion, a first ray extending along the second free end and a second ray extending along the chamfer. The first angle may have a value of between 10 and 90 degrees.

In further embodiments, the first section diameter is configured to control the force required to connect or couple the first component and the second component. Also, the circumferential chamfer may be further defined by a second angle, the second angle having a second vertex where the recess meets the second surface of the second component, a third ray extending along the surface of the second component and a fourth ray extending along the circumferential chamfer. The second angle may have a value of between 10 and 80 degrees.

In another embodiment, them connection mechanism may be akin to a ball-and-collet connection. In some embodiments, the first component may include an elongated member with an end portion having a first diameter. The second component may include a plurality of resilient tabs extending from a base, each of the plurality of tabs having a free end and a side wall extending from the free end to the base. Each free end may further include, or be defined by, a projection extending toward a central axis and terminating at an end portion. The projections defining a circle with a second diameter and an open space. In use, the end portion of the first component may be inserted along the central axis, pressed past the plurality of projections and into the open space. Additionally, selection of the first and second diameters and/or the resiliency of the tabs and/or the shape of the end portion may alter the push-in or pullout force for the first and second components. In certain embodiments, the end portion may be spherical. In other embodiments, the end portion may be another shape such as ellipsoidal.

In accordance with one or more features of the present disclosure, in some embodiments, a surgical instrument assembly is disclosed. The surgical instrument assembly including a handle including an elongated body and a first quick-connect feature at a distal end of the handle, a fin punch configured to be inserted into a proximal end of a surgically-prepared tibia, the fin punch including a second quick-connect feature configured to engage with the distal end of the handle, the fin punch further including a first snap-fit connection on a fin punch inferior surface, and a fin punch guide having an inner surface that defines a passageway sized to receive the fin punch and the handle, the fin punch guide further including a second snap-fit connection on a fin punch guide inferior surface and a third snap-fit connection on a fin punch guide superior surface, wherein the third snap-fit connection on the fin punch guide superior surface is configured to mate with the first snap-fit connection on the fin punch.

The surgical instrument assembly may further include a tibia base trial configured to attach to a proximal end of a surgically prepared tibia, the tibia base trial including a fourth snap-fit connection on a tibia base trial superior surface, wherein the fourth snap-fit connection on the tibia base trial is configured to mate with the second snap-fit connection on the fin punch guide inferior surface.

The fin punch guide may also include a fin punch guide tab on an anterior portion of the fin punch guide. Additionally, the fin punch guide tab may be configured to couple with a recess located on the tibia base trial.

In yet further embodiments, the second snap-fit connection on the fin punch guide inferior surface is a male connection and the third snap-fit connection on the fin punch guide superior surface is a female connection. The first snap-fit connection located on the fin punch inferior surface may be a male connection.

In another aspect of the disclosure, the fin punch guide has buttress portions, and/or the fin punch guide and the fin punch are disposable. Additionally, the fin punch guide and the fin punch may be any one of, or a combination of, polymers or metals. The instruments may be manufactured by rapid manufacturing, injection molding or subtractive manufacturing.

In another example of the current disclosure, a surgical instrument assembly is provided including a handle including an elongated body and a quick-connect feature at a distal end of the handle, a fin punch configured to be inserted into a proximal end of a surgically-prepared tibia, the fin punch including a quick-connect feature configured to engage with the distal end of the handle, the fin punch further including a male snap-fit connection on a fin punch inferior surface, a fin punch guide having an inner surface that defines a passageway sized to receive the fin punch and the body of the handle, the fin punch guide further including a male snap-fit connection on a fin punch guide inferior surface and a female snap-fit connection on a fin punch guide superior surface, wherein the female snap-fit connection on the fin punch guide superior surface is configured to mate with the male snap-fit connection on the fin punch, the fin punch guide further including a fin punch guide tab on an anterior portion of the fin punch guide, and a tibia base trial configured to attach to a proximal end of a surgically prepared tibia, the base trial including a female snap-fit connection on a superior surface of the base trial and a recess, wherein the female snap-fit connection on the base trial is configured to mate with the male snap-fit feature on the fin punch inferior surface and the recess is configured to mate with the fin punch guide tab.

In accordance with one or more features of the present disclosure, in some embodiments, a method of surgically preparing a proximal end of a tibia is disclosed. The method includes placing a tibia base trial on a resected surface of a proximal tibia, the tibia base trial having an opening defined therein, connecting a fin punch guide to the tibia base trial, selecting a fin punch for insertion into the patient's tibia, securing the fin punch to a lower end of a handle, inserting the fin punch through an upper end of the fin punch guide, impacting the fin punch into the proximal end of the tibia through the opening of the tibia base trial, contacting the fin punch with a tab located on an anterior side of the fin punch guide, and disconnecting the handle, fin punch and fin punch guide from the tibia base trial.

In some embodiments, the fin punch guide may be secured to the tibia base trial with a second and a fourth snap-fit connection and the fin punch may be secured to the fin punch guide with a first and a third snap-fit connection. Also, the force holding the fin punch and fin punch guide together may be greater than the force holding the fin punch guide to the tibia base trial. Additional steps may include connecting a trial insert and/or a combination of shims and spacers to the tibia base trial.

In certain embodiments, a trial insert and the tibia base trial connect with a snap-fit connection. Additionally, connecting any of the components together may provide an audible and tactile feedback to a user. In an additional embodiment, the fin punch guide tab may further comprise a lever allowing a user to manipulate the fin punch guide tab, and/or the lever may engage an opening on the tibia base trial.

The method may further include wherein the fin punch is configured to disconnect or decouple the fin punch and fin punch guide when the fin punch is fully impacted into the tibia. The method may also further include removing the base trial and implanting a tibia implant. An additional step may include placing bone cement on the surface of the prepared tibia and placing a final implant onto the patient.

Embodiments of the present disclosure provide numerous advantages. For example, the features of the present disclosure provide the surgeon with audible and haptic feedback so the surgeon is aware that the components have been properly secured to each other. In addition, the connection mechanism pullout and insertion forces may be tailored so that, for example, it is easy to couple a tibia trial insert to a spacer, but harder to couple a spacer to a tibia base trial. In addition, the ability to adjust the pullout and insertion forces allows for disconnecting a handle, fin punch and fin punch guide from a prepared tibia, reducing the number of surgical steps in the procedure.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, specific embodiments of the disclosed device will now be described, with reference to the accompanying drawings, in which.

Figure 1:
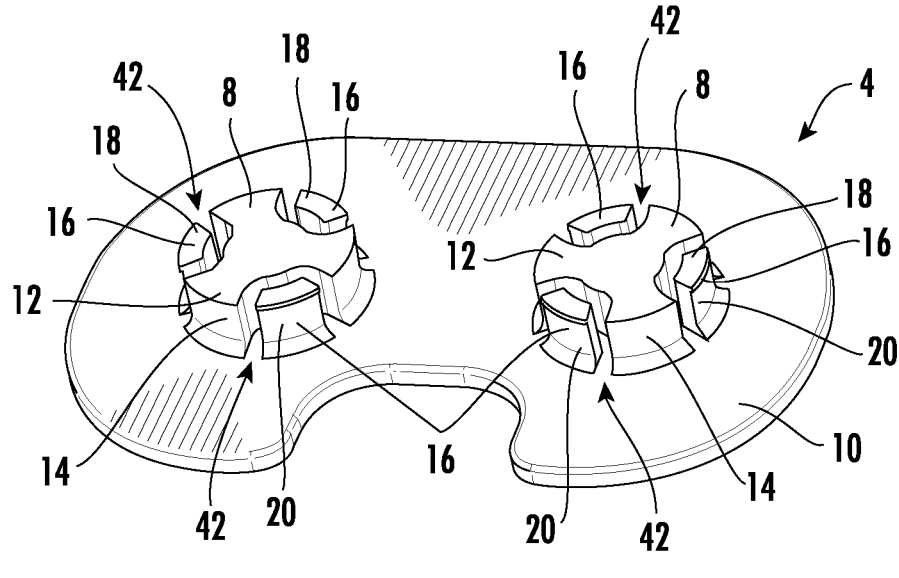
FIG. 1 is a perspective view of a first component including male mating features of a connection mechanism in accordance with one or more features of the present disclosure.

It should be understood that the drawings are not necessarily to scale and that the disclosed embodiments are sometimes illustrated diagrammatically and in partial views. In certain instances, details which are not necessary for an understanding of the disclosed methods and devices, or which render other details difficult to perceive may have been omitted. It should be further understood that this disclosure is not limited to the particular embodiments illustrated herein.

DETAILED DESCRIPTION

Various features of knee instrumentation including one or more mating features will now be described more fully hereinafter with reference to the accompanying drawings, in which one or more features of the instrumentation will be shown and described. It should be appreciated that the various features may be used independently of, or in combination, with each other. It will be appreciated that the mating features and instruments as disclosed herein may be embodied in many different forms and should not be construed as being limited to the embodiments set forth herein. Rather, these embodiments are provided so that this disclosure will convey certain features of the instrumentation and mating features to those skilled in the art. In the drawings, like numbers refer to like elements throughout unless otherwise noted.

As will be described herein, the present disclosure discloses orthopedic instrumentation including, inter alia, improved connection mechanisms to facilitate easier assembly and disassembly. For example, the present disclosure discloses various connection mechanisms for coupling a tibial base trial to a guide (referred to herein as a fin punch guide), and/or for coupling the fin punch guide to a fin punch. In addition, in accordance with one or more features of the present disclosure, an improved method or workflow using the instrumentation will be disclosed. As will be appreciated by one of ordinary skill in the art, a number of connection features and instruments including one or more features may be used in combination or singularly, these features are designed and configured to provide improved connections and a reduction in surgical steps for a surgeon to position and secure an implant on a prepared bone. In addition, while the instrumentation, improved connection mechanisms, and improved workflow will be described in connection with knee implants and trials, the present disclosure should not be so limited as features of the present disclosure may be used in connection with other orthopedic implants, trials, and surgical procedures. As such, the present disclosure should not be so limited unless explicitly claimed.

The instruments described herein may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, nylon, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the instruments and mating components made be produced via a rapid manufacturing process, injection molding or a traditional machining process. In some embodiments, the components may be made for single use. In other embodiments, the components may be sterilized and reused.

In any event, as will be readily apparent from the remaining disclosure, the focus of the present disclosure is on example embodiments of orthopedic instrumentation, including one or more features arranged and configured to provide improved connections between the components. Thus, it should be appreciated that the present disclosure should not be limited to any particular configuration of instrumentation having any particular configuration unless specifically claimed.

Referring to FIGS. 1-4, a first embodiment of a connection mechanism is disclosed. FIG. 1 illustrates a first component 4, which is a simplified embodiment of a trial component that, in use, may be placed on the proximal end of a resected tibia (not shown) as would be readily appreciated by one of ordinary skill in the art. As illustrated, the first component 4 includes a first surface 10 and a second surface opposite the first surface 10. The connection mechanism includes a boss 8 and a plurality of tabs 16 extending from the first surface 10 (e.g., illustrated extending in a superior direction from the first surface 10 of the first component 4). The boss 8 including a first side wall 14 and a first free end 12. The plurality of tabs 16 including a second side wall 20 and a second free end 18. As illustrated in FIG. 1, in some embodiments, the first component 4 may include first and second connection mechanisms. In addition, each connection mechanism may include one boss 8 and three tabs 16. However, this is but one configuration and the first component 4 may include more or less connection mechanisms including one, three, four, or more, and each connection mechanism may include more or less bosses 8 and/or more or less tabs 16. As illustrated, a space 42 separates the boss 8 from each of the plurality of tabs 16 (e.g., a space 42 is provided between the outer surface of the boss 8 and the inner surface of the tab 16). As will be described herein, the space 42 enables the tabs 16 to deflect. The boss 8 prevents the tabs 16 from over deflecting (e.g., boss 8 and/or space 42 controls the amount of permitted tab deflection).

Figure 2A:
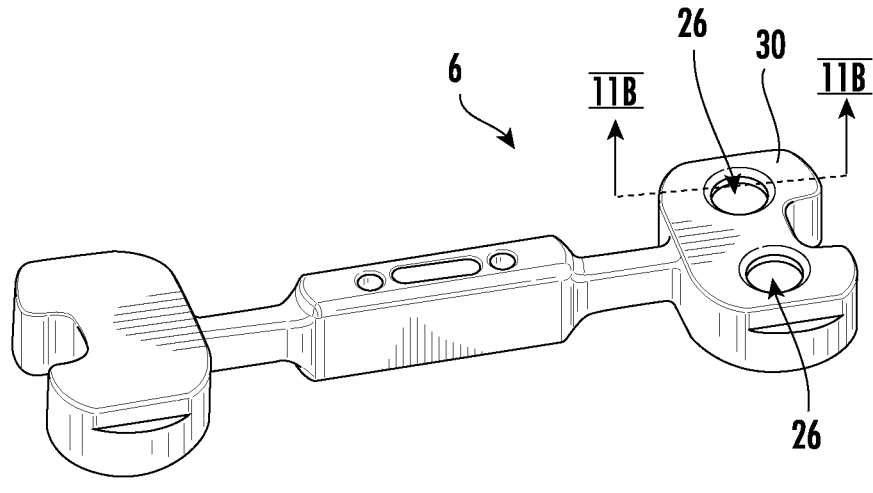
FIG. 2A is a perspective view of a second component including female mating features of the connection mechanism in accordance with one or more features of the present disclosure, the female mating features being arranged and configured to receive the male mating of FIG. 1.
Figure 2B:
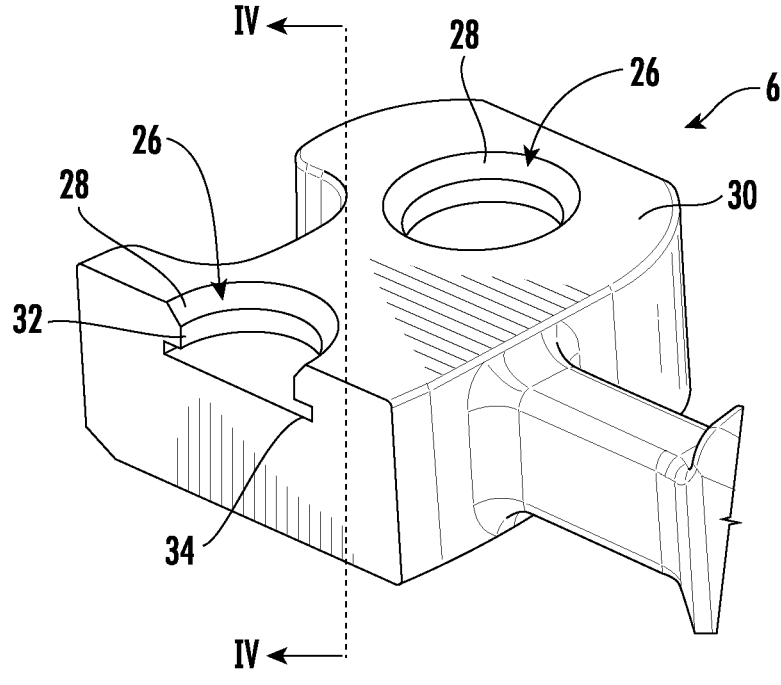
FIG. 2B is a partial cross-sectional view of the second component shown in FIG. 2A taken through line IIB-IIB in FIG. 2A.

FIGS. 2A and 2B illustrate an embodiment of a second component 6 arranged and configured to mate or couple with the first component 4. FIG. 2. Illustrates the second component 6 in the form of a trial spacer, although this is but one configuration. As illustrated, the second component 6 includes a second surface 30 and a plurality of recesses 26 extending into second component 6. In use, the first component 4 and the second component 6 include a corresponding number of connection mechanisms (e.g., a corresponding number of tabs 16 and bosses 8 on the first component 4 and recesses 26 on the second component 6), which in the embodiment shown is two, although this is but one configuration and more or less connection mechanisms may be used. In addition, as will be appreciated, the first component 4 may include recesses and the second component 6 may include tabs and bosses.

In some embodiments, the recess 26 may include a circumferential chamfer 28. In this particular embodiment, the circumferential chamfer 28 extends around the entire recess 26; however, partial chamfers are also envisioned. Adjacent to the circumferential chamfer 28 and extending farther into the recess 26 may be a first section 32. As illustrated, the recess 26 and the first section 32 may have a circular shape; however, this embodiment is merely exemplary and not meant to limit the scope of the disclosure. Other shapes such as elliptical, square, rectangular, etc. are envisioned. Adjacent the first section 32 may be a second section 34. As illustrated, the second section 34 may have a complementary shape as the first section 32, which in the illustrated embodiment is a circular shape; however, the second section 34 may have a slightly larger diameter than the first section 32 for reasons that will become apparent. Again, other shapes for the second section 34 are envisioned such as, for example, elliptical, square, rectangular, etc.

In use, the connection mechanism (e.g., the tabs 16, boss 8, and recesses 26) shown in FIGS. 1 and 2 can be mated together to connect the first component 4 to the second component 6. In this regard, the connection mechanism may be akin to, and referred to herein, as a snap-fit connection for coupling first and second components 4, 6. In addition, such connection can produce tactical feedback including an audible sound and feel. In use, the boss 8 and tabs 16 of the first component 4 are aligned with and inserted into the recess 26 of the second component 6. As the tabs 16 contact the circumferential chamfer 28 formed in the recess 26, the tabs 16 deflect, closing the space 42. Any or all parts of the first component 4 and/or the second component 6 may be made of a resilient material such as a polymer or metal to allow the tabs 16 to flex or bend. As the tabs 16 are urged further into the recess 26, they eventually align with the second section 34 of the recess 26. Given the larger diameter of the second section 34, the tabs 16 are free to return to their original positions or to a partially bent position. At this point, an audible noise may be produced from the tabs 16 returning to their unstressed or partially stressed positions and the two components are connected.

Figure 3A:
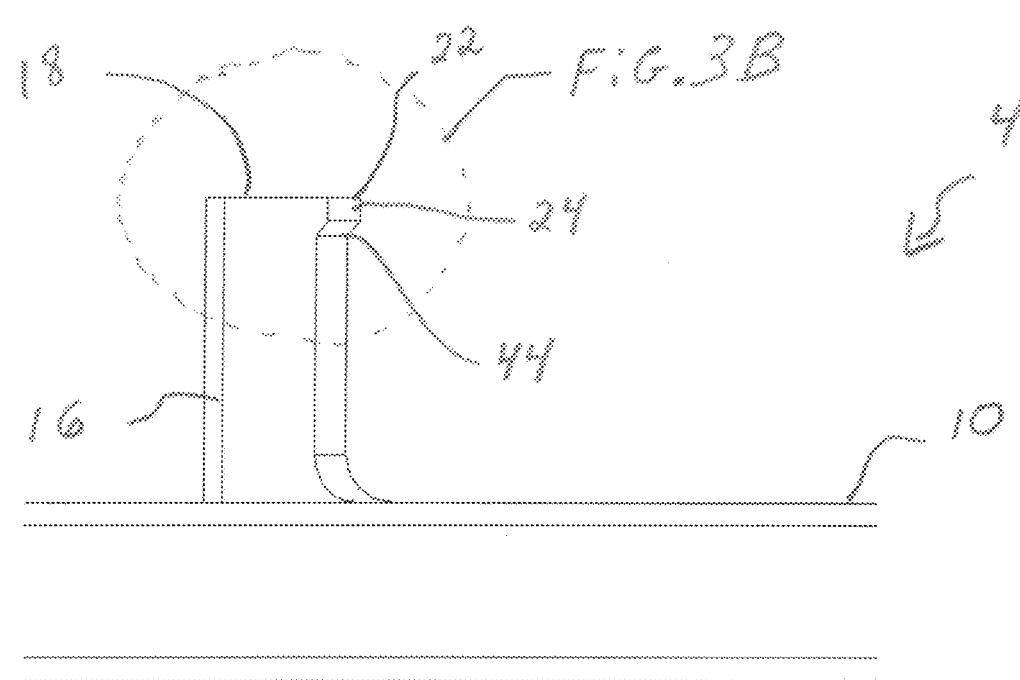
FIG. 3A is a detailed, side view of a portion of the male mating feature shown in FIG. 1.
Figure 3B:
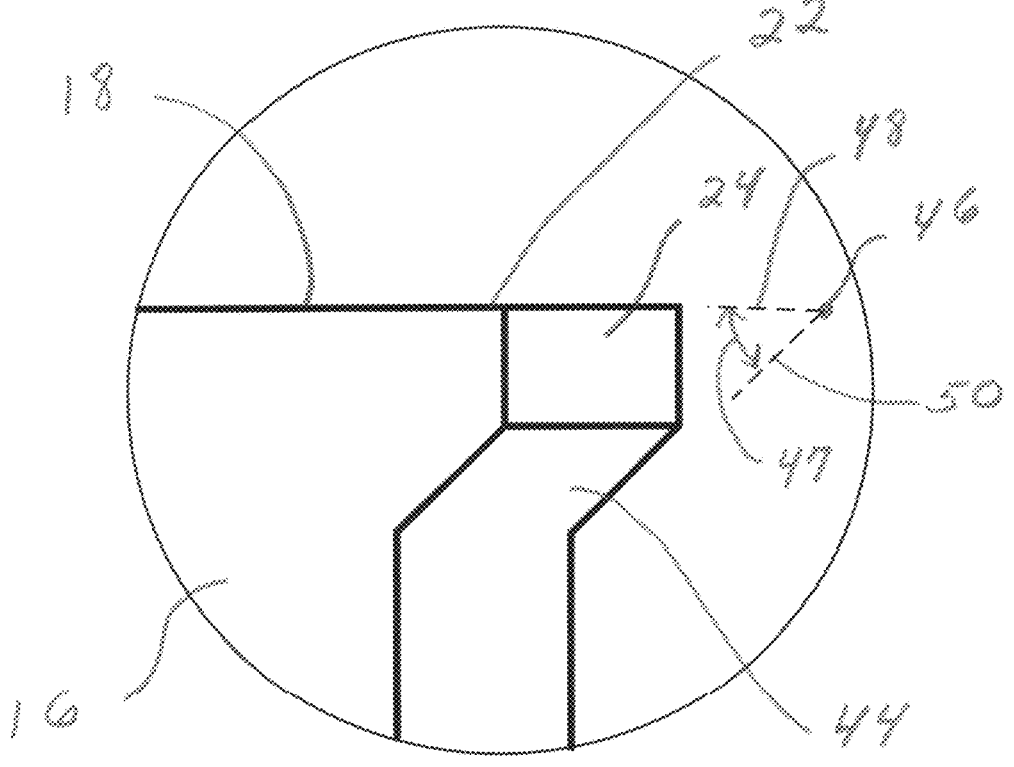
FIG. 3B is a detailed view of the portion of the male mating feature shown in FIG. 3A.

With additional reference to FIGS. 3A and 3B, the tabs 16 may include a projection 22, which is arranged and configured to fit into the second section 34 of the recess 26 preventing the components from separating. It should be appreciated that the shape of the boss 8, tabs 16 and recess 26 are not critical to this disclosure, and other shapes like ovals, squares, hexagons, and the like are envisioned. The number of tabs 16 is also not critical to this disclosure. The particular material chosen for the first component 4 and the second component 6 is also not critical, as long as the tabs 16 are able to bend in response to an externally applied force.

Also, in an embodiment where the tabs 16 are inserted into the second section 34 in an unstressed state, there may be some space between the projection 22 and the second section 34. This space may define a maximum acceptable degree of slop, or looseness between the fit of the first component 4 and the second component 6. One of ordinary skill in the art can recognize there may be instances where some slop is warranted and other instances when very little to no slop is warranted. In the latter instance, the tabs 16 should be partially stressed within the second section 34.

Figure 4:
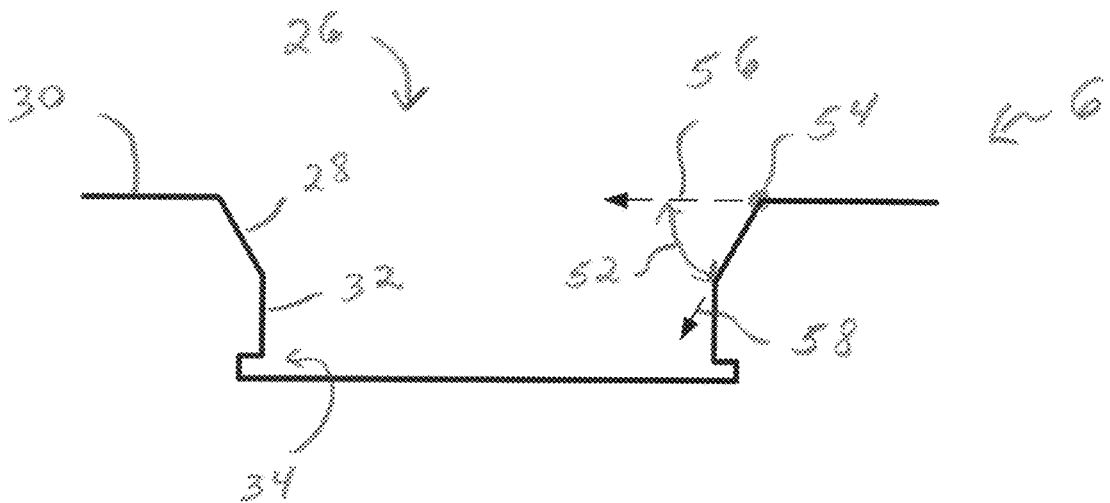
FIG. 4 is a cross-sectional view of the second component shown in FIG. 2B taken along line IV-IV in FIG. 2B.

FIGS. 3A, 3B, and 4 illustrate ways in which the embodiments shown in this disclosure may be tailored to meet other design requirements. By way of definition, the push-in force is the amount of force a user needs to connect the first component 4 to the second component 6 and the pull-out force is the amount of force a user needs to disconnect the first component 4 from the second component 6.

FIG. 3A is a side view of the tab 16 shown in FIG. 1. In use, the design of the tab 16 dictates the pull-out force needed to separate the first component 4 from the second component 6. As illustrated in FIG. 3A, in some embodiments, the tab 16 includes a projection 22 extending from the second free end 18 thereof. The projection 22 may include an end portion or face 24 and a chamfer 44. As shown in FIG. 3B, the chamfer 44 may be defined by an angle 47, formed from a first ray 48 and a second ray 50 intersecting at a vertex 46. In practice, the first ray 48 is a line that can be drawn on and extending from or along the second free end 18 and the second ray 50 is a line that can be drawn on and extending from or along the chamfer 44. When angle 47 is increased, the pull-out force is decreased. When angle 47 is decreased, the pull-out force is increased. In use, angle 47 may be anywhere between 0 and 90 degrees; however, a more preferred range is 10-80 degrees, more preferably between 30 to 60 degrees, and more preferably between 40 and 50 degrees.

FIG. 4 is a cross-sectional view taken through the second component 6 along line IV-IV shown in FIG. 2 and illustrates an embodiment of the recess 26. In particular, FIG. 4 illustrates how the first section 32 and the circumferential chamfer 28 may be configured to tailor the push-in force. As seen in FIG. 4, an angle 52 may be formed by the intersection of a third ray 56 and a fourth ray 58 at a second vertex 54. In practice, the third ray 56 may be a line extending from or along the second surface 30 and the fourth ray 58 may be a line that extending from or along the circumferential chamfer 28. By increasing the diameter of the first section 32, the push-in force is decreased and by decreasing the diameter of the first section 32, the push-in force may be increased. The angle 52 also tends to control how quickly the push-in force ramps up for the initial deflection to the maximum deflection of the tabs 16. The angle 52 may be anywhere between 0 and 90 degrees; however, a more preferred range is 10-80 degrees, more preferably between 30 to 60 degrees, and more preferably between 40 and 50 degrees.

Figure 5:
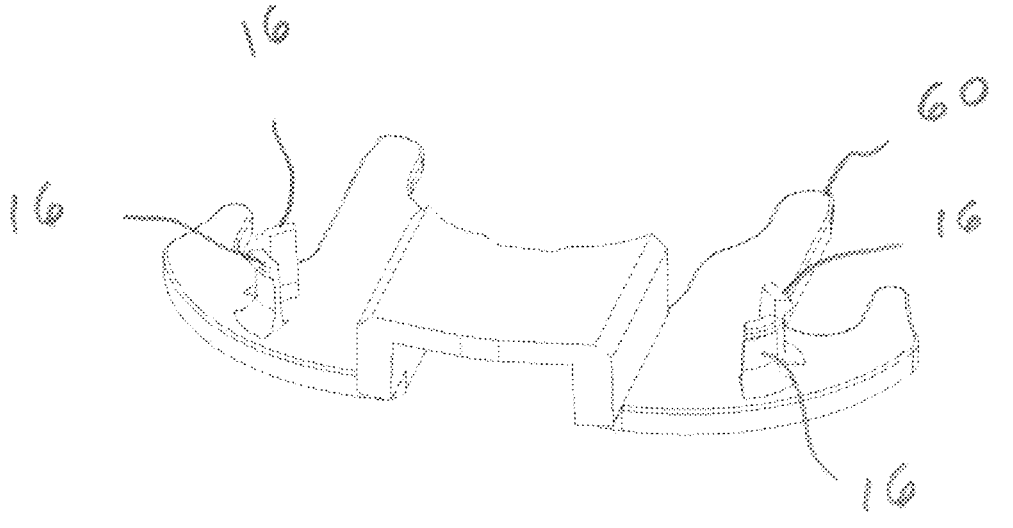
FIG. 5 is a perspective view of an embodiment of a spacer or a tibia shim illustrating an alternate embodiment of a male mating feature in accordance with one or more features of the present disclosure.
Figure 7A:
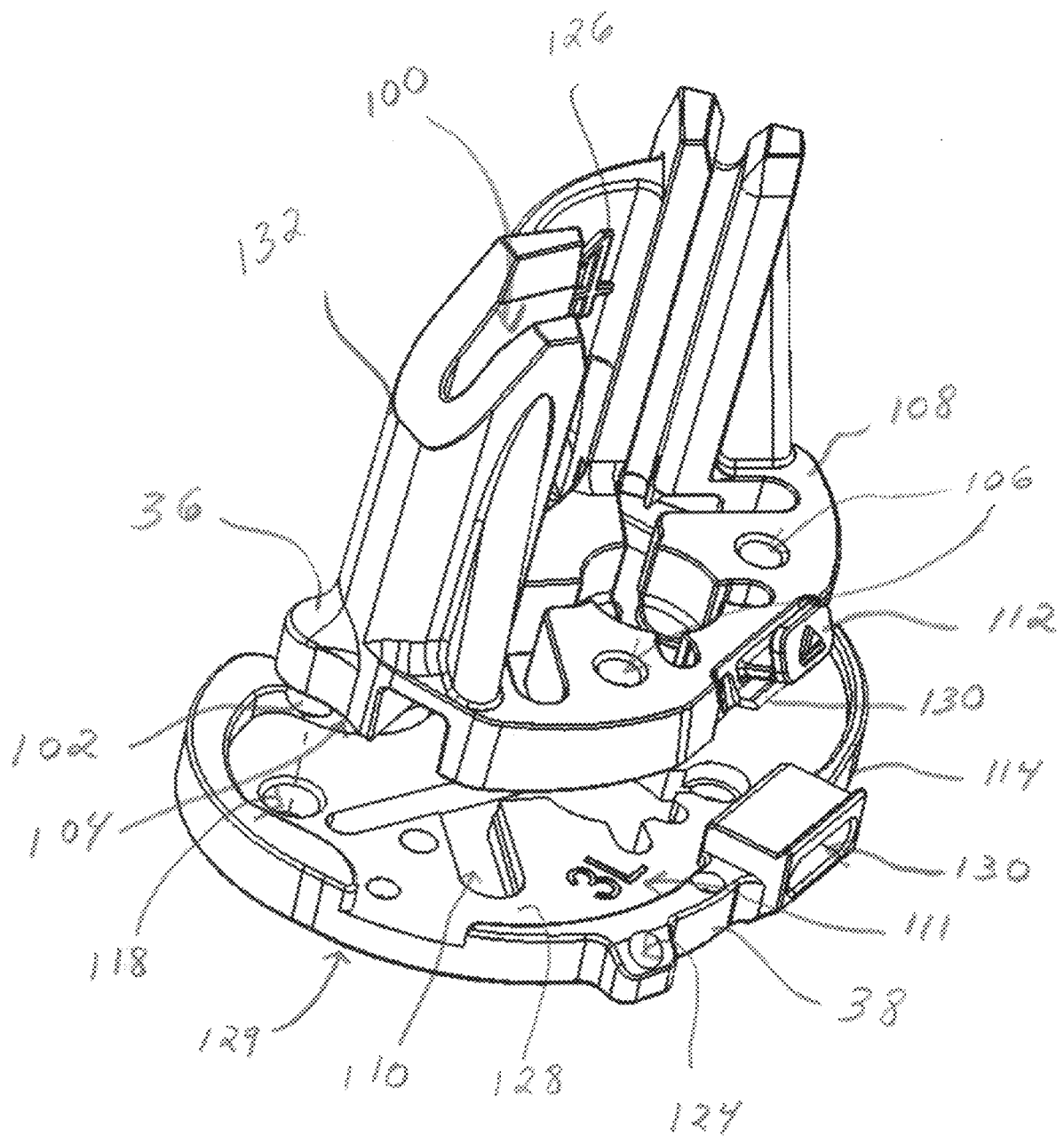
FIG. 7A is a perspective view of a fin punch guide located adjacent to a tibia base trial.
Figure 7B:
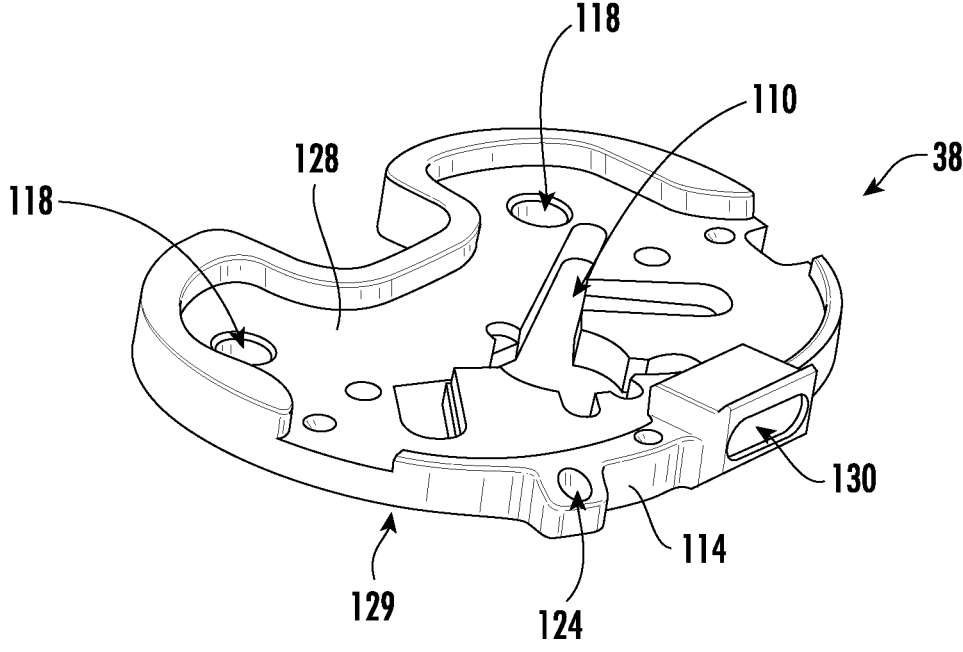
FIG. 7B is a perspective view of the tibia base trial shown in FIG. 7A.
Figure 13A:
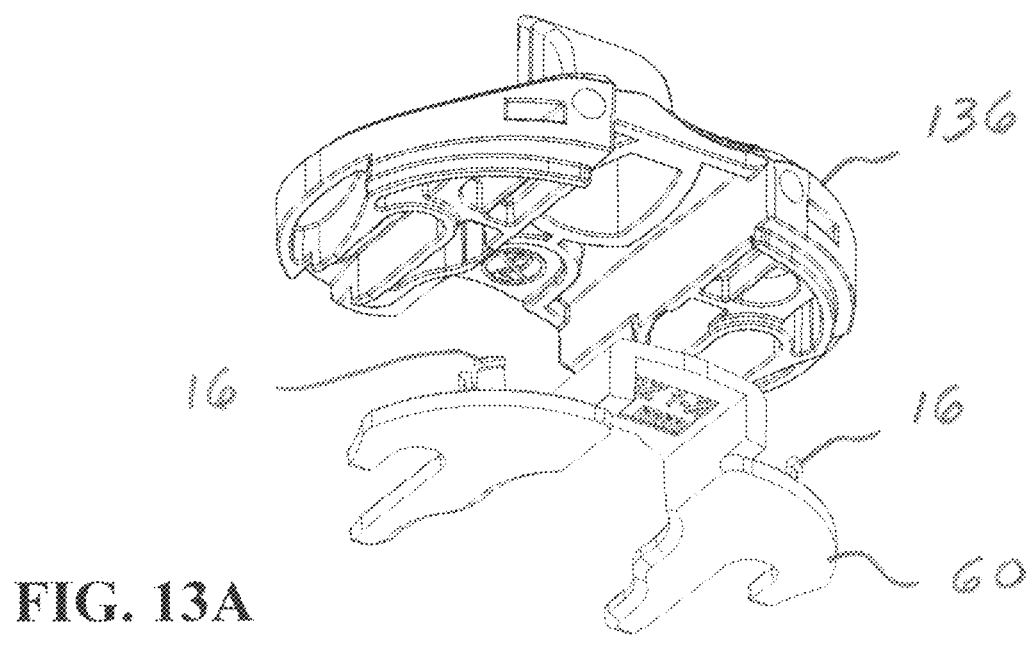
FIGS. 13A and 13B are perspective views of a spacer and a tibia trial insert showing a connection mechanism in accordance with one or more features of the present disclosure.
Figure 13B:
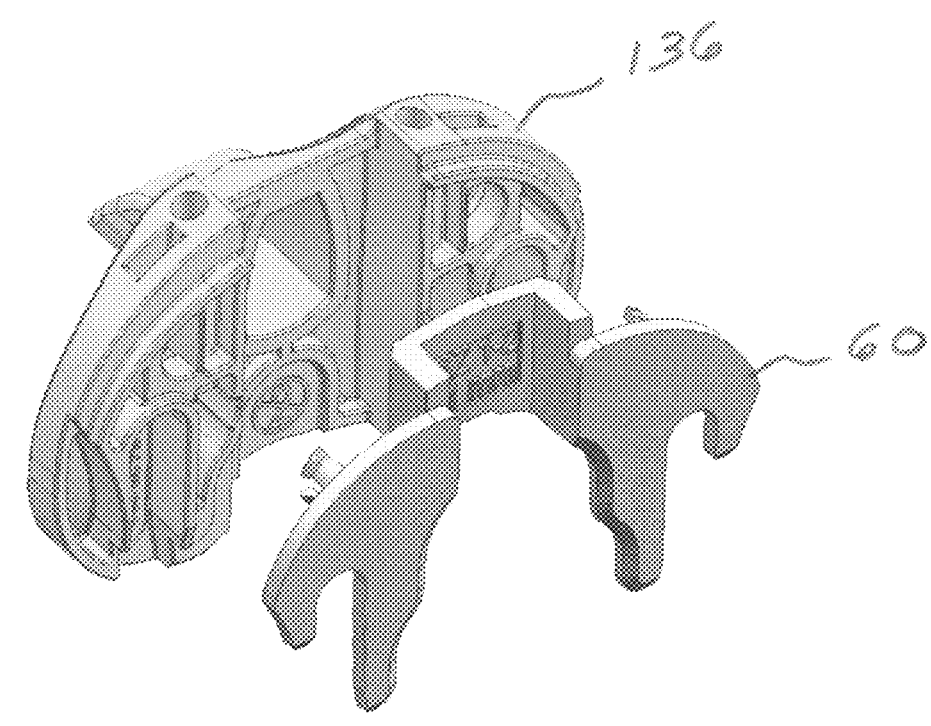

FIG. 5 illustrates another embodiment in accordance with one or more features of the present disclosure showing for simplicity only a few tabs 16 formed on a tibia shim or spacer 60. In use, as will be readily appreciated by one of ordinary skill in the art, the spacer 60 may be used in a surgery to increase the height of a tibia trial component. In use, the spacer 60 may be stacked on top of a tibia base trial (example embodiments of which are shown in FIGS. 7A and 7B) as an intermediate component between a tibia base trial and an articular insert (example embodiments of which is shown in FIGS. 13A and 13B). As illustrated in FIG. 5, the male mating or connection feature of the connection mechanism may only include two tabs 16, although more or less tabs 16 may be utilized. In addition, as illustrated, the male mating or connection feature of the connection mechanism may not include a boss 8, which was shown in connection with the previous embodiment and the boss 8 may not be necessary in some embodiments of this disclosure.

Figure 6:
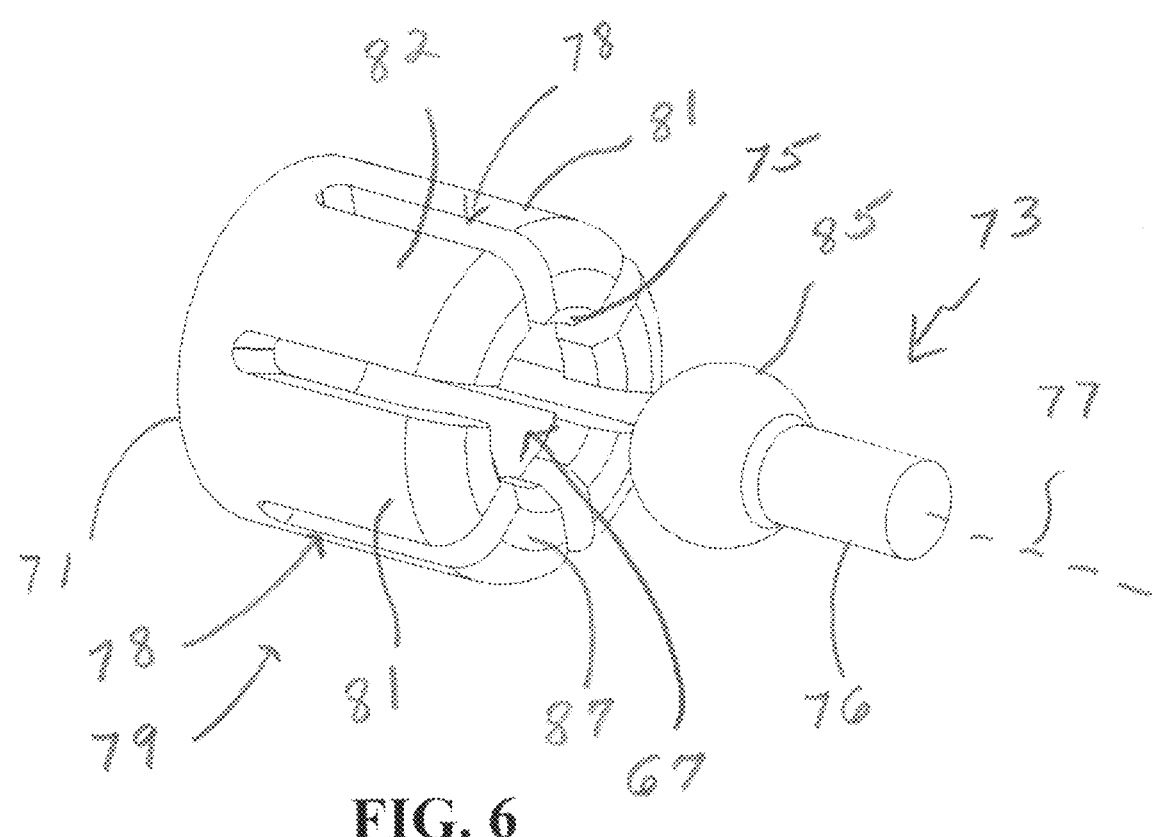
FIG. 6 is a perspective view of an alternate embodiment of a connection mechanism including male and female mating features in accordance with one or more features of the present disclosure.

FIG. 6 illustrates an alternate embodiment of a connection mechanism that may be used in accordance with one or more features of the present disclosure. In use, the connection mechanism may be used in combination with or separately from, the other connection mechanisms disclosed herein. In this embodiment, the first component 73 includes an elongated member 76 such as, for example, a shaft, with an enlarged end portion 85. In some embodiments, the end portion 85 may include a spherical shape having a first diameter. For example, the end portion 85 may have an enlarged ball-shaped end or tip portion.

The second component 79 may include a base 71, a plurality of resilient tabs 81 extending from the base 71, and an interior cavity 67 arranged and configured to receive the end portion 85 of the first component 73. In this regard, the connection mechanism may be akin to, and referred to herein, as a ball and collet connection for coupling first and second components. As in the previous embodiment, each of the plurality of tabs 81 may include a free end 87 and a side wall 82 extending from the base 71 to the free end 87. In addition, the free end 87 of each tab 81 may include a projection 75 extending toward a central axis 77. In use, the projections 75 define a circle with a second diameter. As illustrated, the second component 79 may include a plurality of slots 78 formed in the side wall 82. In use, as will be readily appreciated by one of ordinary skill in the art, the slots 78 enable the plurality of tabs 81 to flex to receive the end portion 85 of the elongated member 76 associated with the first component 73. In use, the end portion 85 of the first component 73 (e.g., ball-shaped end portion) may be inserted along the central axis 77 and pressed or inserted past the plurality of projections 75 and into the interior cavity 67 of the second component 79. Similar to the previous embodiment, selection of the first and second diameters and/or the resiliency of the tabs 81 and/or the shape of the free end 87, and/or the shape and size of the end portion 85 may alter the push-in or pullout force for first and second components 73, 79, respectively. In the embodiment shown, the end portion 85 is spherical, but in other embodiments, the end portion may be provided in alternate shapes such as, for example, ellipsoidal, oval, etc. Also, for clarity FIG. 6 only shows the connection mechanism, not the instruments or components (i.e., tibia base trial, spacers, etc.) that form the first and second components 73, 79 (e.g., the components which the elongated member 76 and base 71 are coupled to, formed with, etc.).

With reference to FIGS. 7A-12 an exemplary system and method illustrating the steps of tibia preparation in connection with a total knee arthroplasty in accordance with one or more features of the present disclosure will now be described. In accordance with one or more features of the present disclosure, in some embodiments, the exemplary system and method may utilize one more connection mechanisms for coupling various components. For example, the components may utilize the snap-fit connection mechanism previously described in connection with FIGS. 1-5, the ball and collet connection mechanism previously described in connection with FIG. 6, or any of the other connection mechanisms disclosed later herein, or any combination thereof including incorporation of one or more now known or hereafter developed connection mechanisms. Thus arranged, in use, the first and second components may be coupled to each other utilizing, inter alia, a quick connect mechanism.

Figure 7C:
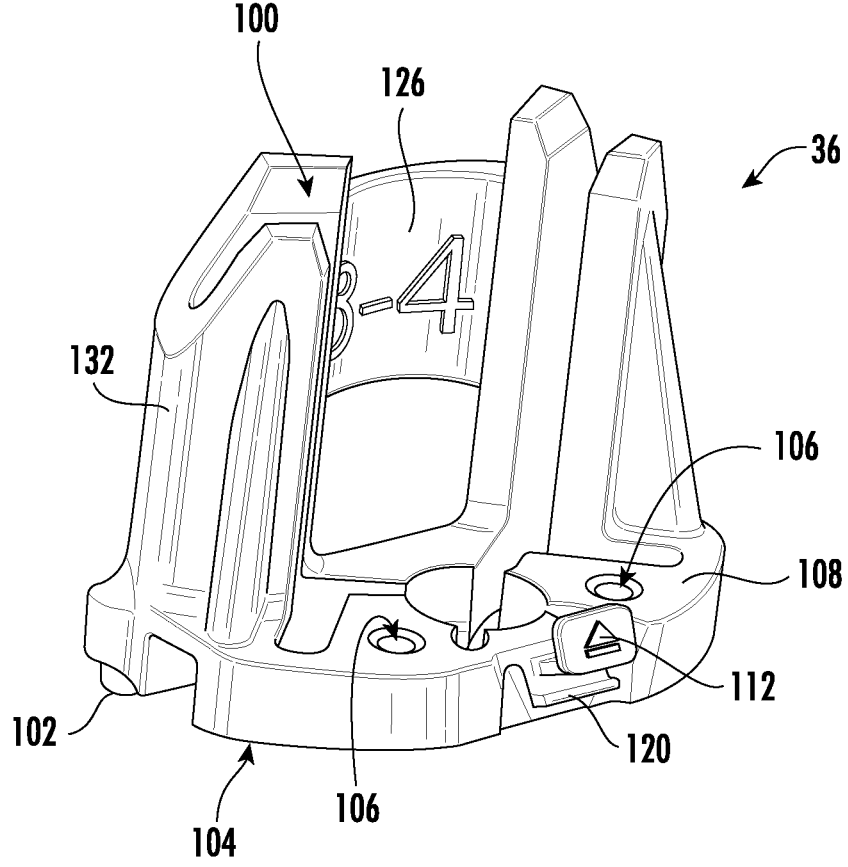
FIG. 7C is a perspective view of the fin punch guide shown in FIG. 7A.

FIG. 7A is a perspective view of an embodiment of a fin punch guide 36 and a tibia base trial 38 in accordance with one or more features of the present disclosure. FIG. 7B is a perspective view of the tibia base trial 38. FIG. 7C is a perspective view of the fin punch guide 36.

As illustrated, the fin punch guide 36 includes a superior surface 108, an inferior surface 104, and buttress portions 132 extending from the superior surface 108. A passageway 100 is formed within the buttress portions 132. Similarly, the fin punch guide 36 includes a passageway 110 corresponding to the passageway 100 formed in the buttress portion 132. In use, the passageways 100, 110 are sized and configured to allow the passage, insertion, etc. of a fin punch 40 (shown in FIGS. 10A and 10B) through the fin punch guide 36, through the tibia base trial 38 and into a patient's tibia to form, for example, an opening, a cut, or the like to receive a keel or stem portion of an orthopedic tibia implant. The fin punch 40 may be provided in several sizes based upon patient anatomy, as such, the fin punch guide 36 may include a size indicator 126 to enable a user to select the proper sized fin punch 40 for the procedure being performed.

The fin punch guide 36 may also be provided with one or more connection mechanisms as previously described or as will be described herein for coupling the fin punch guide 36 to the tibial base trial 38. For example, the fin punch guide 36 may include a connector 102 such as, for example, a male mating or coupling feature extending from the inferior surface 104 arranged and configured to mate or couple with a female mating or coupling feature 118 formed in the tibial base trial 38, although this is but one configuration and the fin punch guide 36 may include the female mating or coupling feature and the tibial base trial 38 may include the male mating or coupling feature. In some embodiments, the male mating or coupling feature may include the tabs 16 and/or boss 8 and the female mating or coupling feature may include the corresponding recess 26 described above in connection with the snap-fit connector described in connection with FIGS. 1-4 and 5. Alternatively, in some embodiments, the male mating or coupling feature may include the enlarged end portion 85 and the female mating or coupling feature may include the collet described above in connection with the ball and collet connector described in connection with FIG. 6. Although the second connector 102 is shown as a single male connection, this disclosure is not construed to be limiting, and the connection may be single or multiple male or female connections.

In addition, as illustrated, the fin punch guide 36 may one or more connection mechanisms as previously described or as will be described herein for coupling the fin punch guide 36 to the fin punch 40. For example, the fin punch guide 36 may include one or more connectors 106 such as, for example, a female mating or coupling feature formed in the superior surface 108 thereof arranged and configured to mate or couple with a male mating or coupling feature 96 formed in the fin punch 40, although this is but one configuration and the fin punch guide 36 may include the male mating or coupling feature and the fin punch 40 may include the female mating or coupling feature. In some embodiments, the male mating or coupling feature may include the tabs 16 and/or boss 8 and the female mating or coupling feature may include the corresponding recess 26 described above in connection with the snap-fit connector described in connection with FIGS. 1-4 and 5. Alternatively, in some embodiments, the male mating or coupling feature may include the enlarged end portion 85 and the female mating or coupling feature may include the collet described above in connection with the ball and collet connector described in connection with FIG. 6. Although the connector 106 is shown as a single female connection, this disclosure is not construed to be limiting, and the connection may be single or multiple male or female connections. In addition, as will be described in greater detail below, the fin punch guide 36 may include a fin punch guide tab 112 provided on the anterior side thereof.

With reference to FIGS. 7A and 7B, the tibia base trial 38, which is arranged and configured to reside on a resected surface of a patient's tibia, includes a trial superior surface 128 and a trial inferior surface 129. As previously mentioned, a passageway 110 is formed within the tibia base trial 38, the passageway 110 being arranged and configured to allow a particular size of fin punch 40 to pass therethrough and into the patient's tibia. Similar to the fin punch guide 36, the tibia base trial 38 may be available in a number of sizes and thus may include a size indicator 111. In the embodiment shown in FIG. 7A, the size indicator indicates a size 3, left tibia. In addition, the tibia base trail 38 may include one or more fixation pin openings 124 arranged and configured to enable a surgeon to pin the tibia base trial 38 to a patient's tibia.

As illustrated, and as previously mentioned, the tibia base trial 38 may also include one or more connectors 118 arranged and configured to mate with the connector 102 formed on the fin punch guide 36 to quickly connect the fin punch guide 36 to the tibial base trial 38. Although the connector 118 is shown as a single female connection, as previously disclosed, this disclosure is not construed to be limiting, and the connection may be single or multiple male or female connections. In use, and as previously described, the connectors 102, 118 may be arranged and configured to mate together as described in FIGS. 1-5. As further illustrated, in some embodiments, the tibia base trial 38 includes an anterior side 114 with a trial recess 130 formed therewith for reasons that will be described below.

Figure 8:
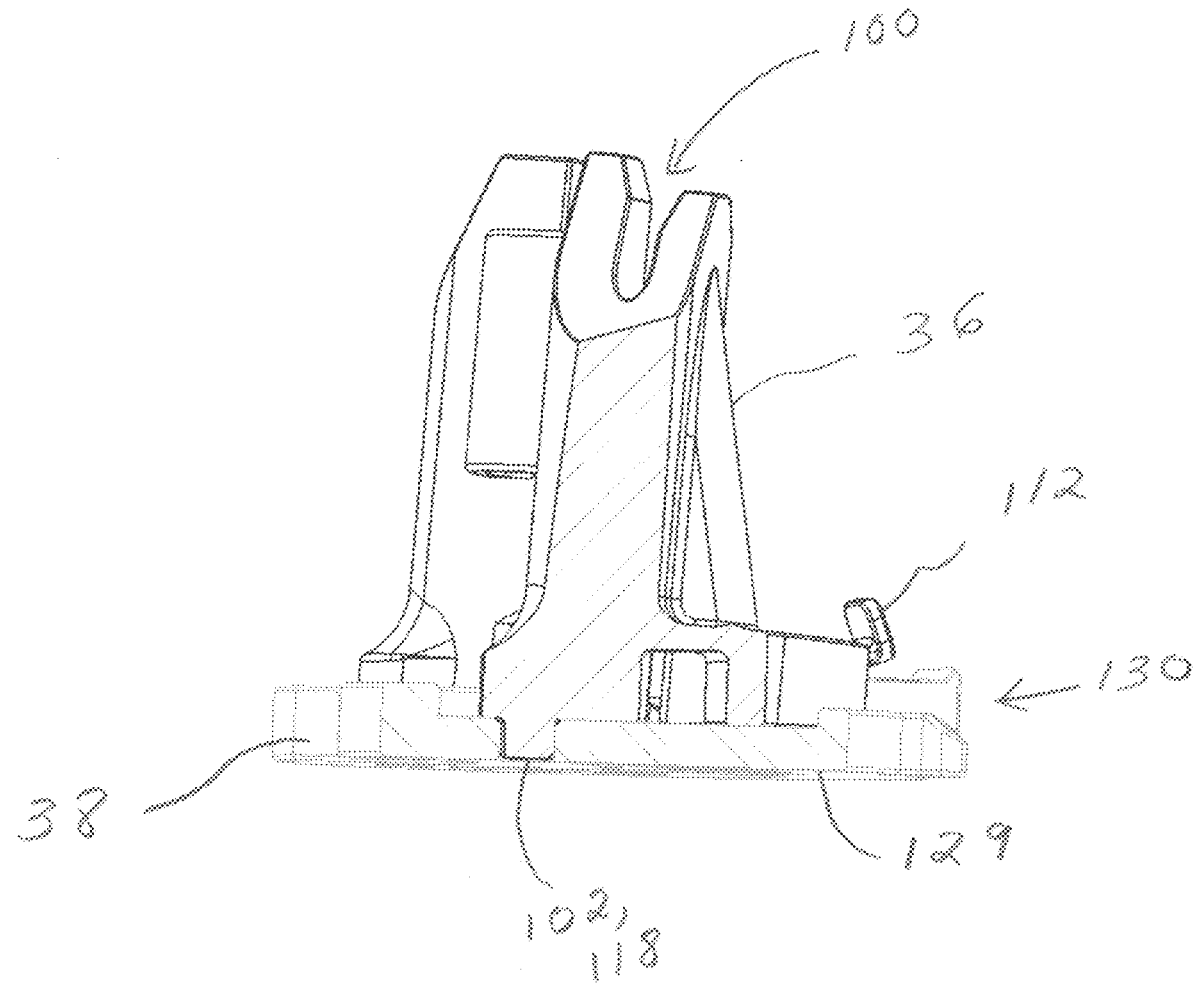
FIG. 8 is a side view of a fin punch guide connected to a tibia base trial.
Figure 9:
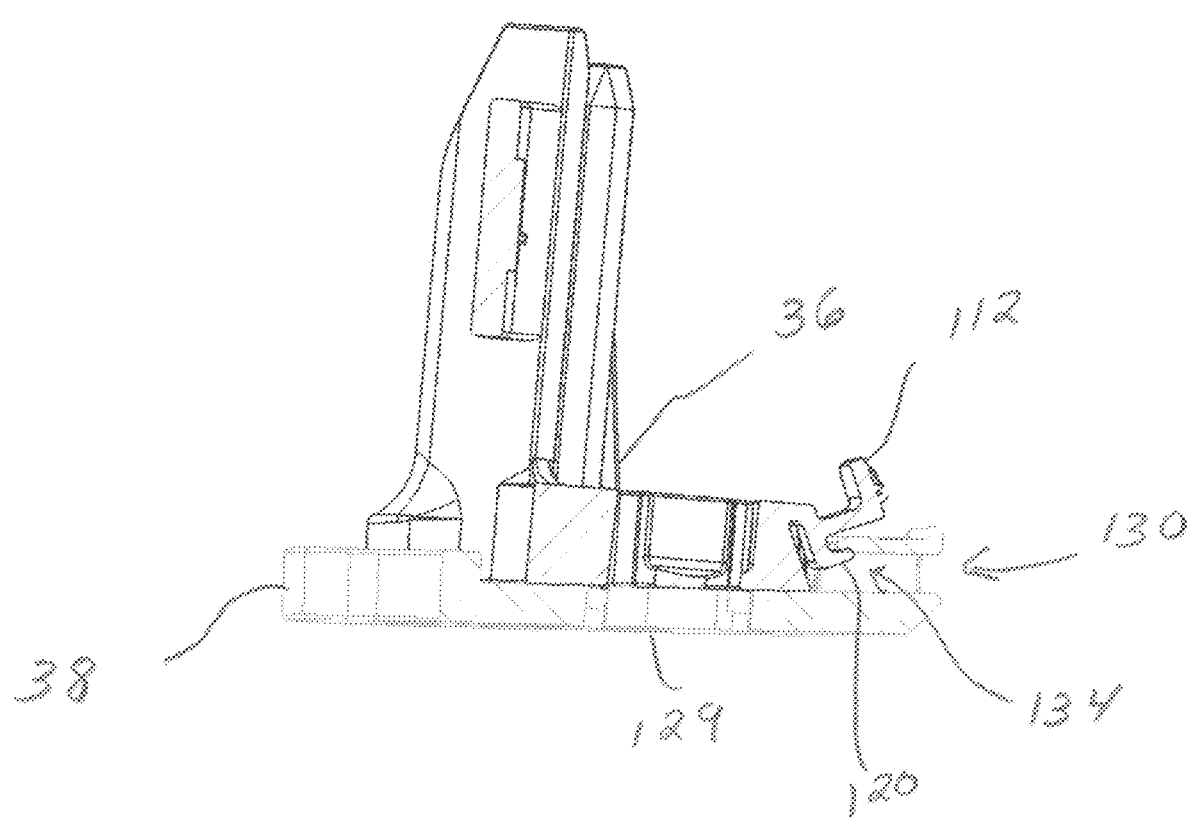
FIG. 9 is an additional side view of a fin punch guide and tibia base trial connected together.

FIGS. 8 and 9 illustrate an intermediate step in preparing a patient's tibia. As illustrated in FIGS. 8 and 9, the fin punch guide 36 has been coupled to the tibia base trial 38 using, for example, one or more of the connection mechanisms described herein. In addition, as illustrated, the fin punch guide tab 112 may include a lever or hook-shaped end portion 120. As illustrated, with the fin punch guide 36 coupled to the tibial base trial 38, the lever 120 rests within the recess 130 formed in the tibia base trial 38, with the lever or hook-shaped end portion 120 engaging a recessed surface 134 formed within the recess 130. Thus arranged, additional securement for coupling the fin punch guide 36 to the tibial base trial 38 is provided.

Figure 10A:
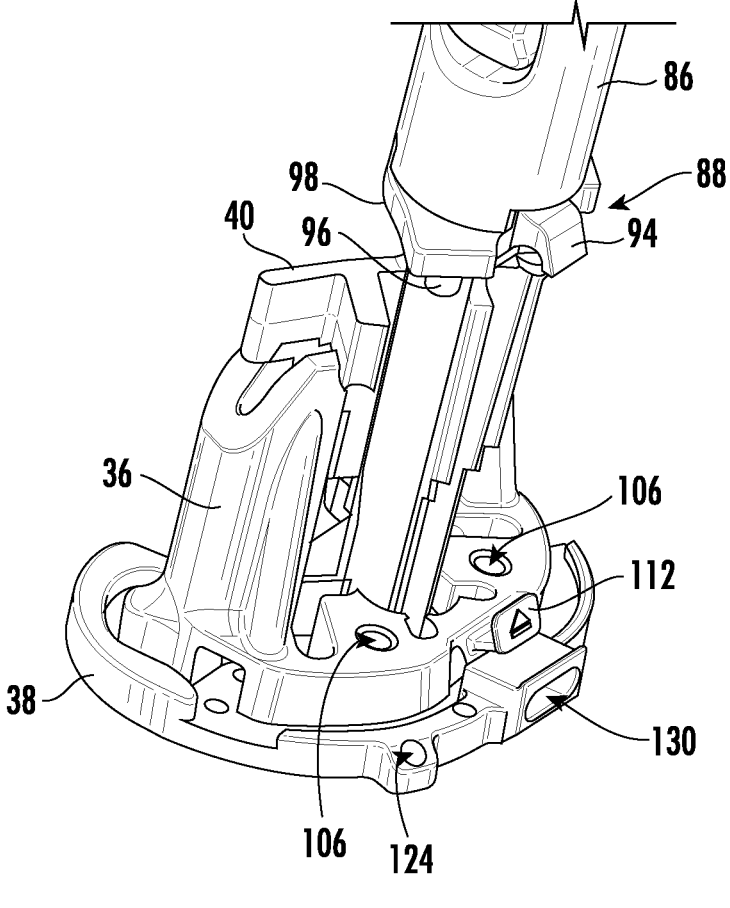
FIG. 10A is a perspective view of an assembled fin punch guide and tibia base trial with a fin punch and handle positioned above the assembly.
Figure 10B:
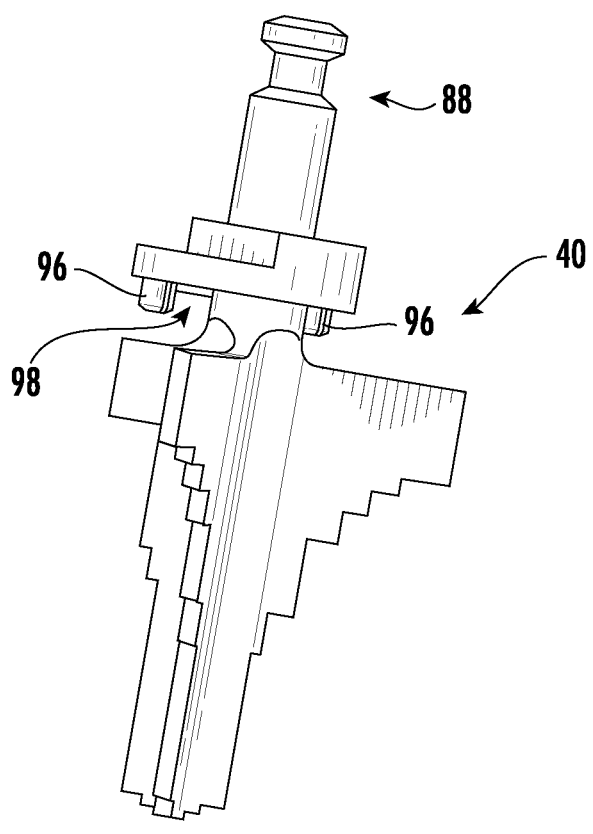
FIG. 10B is a perspective view of the fin punch shown in FIG. 10A.
Figure 11:
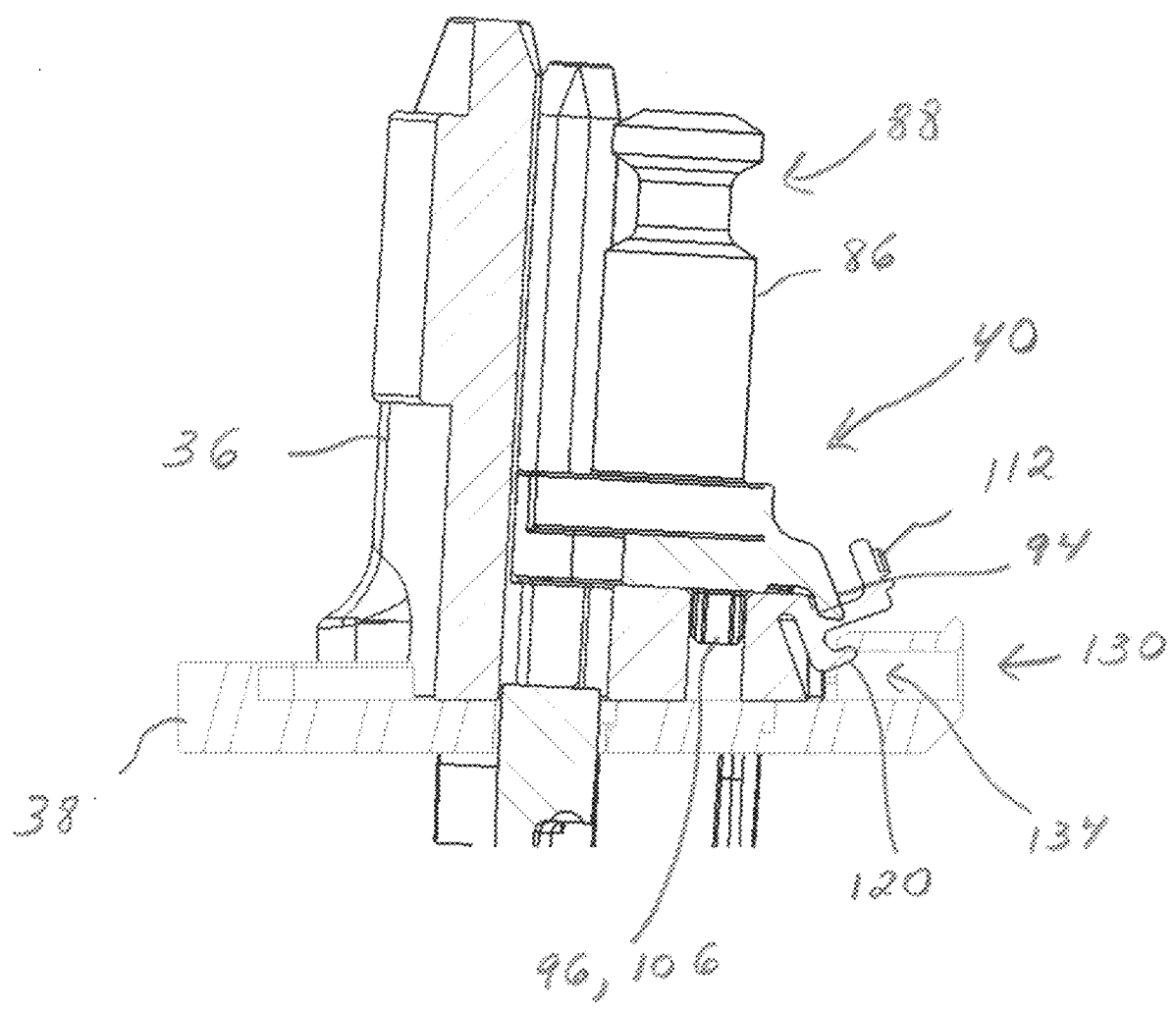
FIG. 11 is a side view of an assembled fin punch guide and tibia base trial with a partially inserted fin punch.

Next with reference to FIGS. 10A and 10B, a user selects the proper sized fin punch 40 and assembles it to a handle 86 using, for example, a quick-connect mechanism 88 formed on the fin punch 40, although this is but one configuration and any suitable connection mechanism now known or hereafter developed may be utilized including, for example, a blade, a bayonet, a Jacobs-Hall, etc. In use, the fin punch 40 includes a fin punch inferior surface 98 and disposed on the fin punch inferior surface is one or more connectors 96 arranged and configured to mate or couple with the one or more connectors 106 formed on the fin punch guide 36 for coupling the fin punch 40 to the fin punch guide 36. As previously described, although the connector 96 is shown as a single male connection, this disclosure is not construed to be limiting, and the connection may be single or multiple male or female connections for any of the embodiments described herein.

The remaining steps in the surgical technique for preparing a patient's tibia are illustrated with reference to FIGS. 10A-12. After the patient's tibia has been resected and the size of the tibia base trial 38 has been selected, the tibia base trial 38 may be pinned to the patient's resected bone using fixation pins and the one or more fixation pin openings 124 formed in the tibia base trial 38. Next, the proper sized fin punch guide 36 is selected and is connected to the tibia base trial 38 via corresponding connectors 102, 118 as previously described.

Next, the proper sized fin punch 40 is selected and assembled to the handle 86. Then the fin punch 40 is guided through the passageway 100 formed in the fin punch guide 36, through the passageway 110 formed in the tibial base trial 38, and into the patient's tibia. There will typically be a strike plate on the end or top of the handle 86 to allow a user to use a hammer or the like to drive the fin punch 40 into the patient's bone.

As the fin punch 40 is driven deeper into the patient's bone, the fin punch inferior surface 98 approaches the superior surface 108 of the fin punch guide 36. Eventually, the connector 106 formed on the fin punch guide 36 engages the connector 96 formed on the fin punch 40 thereby coupling the fin punch 40 to the fin punch guide 36. In doing so, a release 94, which may be arranged and configured as a depending projection formed on the fin punch 40 contacts the fin punch guide tab 112. In doing so, the release 94 pushes down on the fin punch guide tab 112 until the lever 120 releases the recess surface 134 associated with the trial recess 130.

Figure 12:
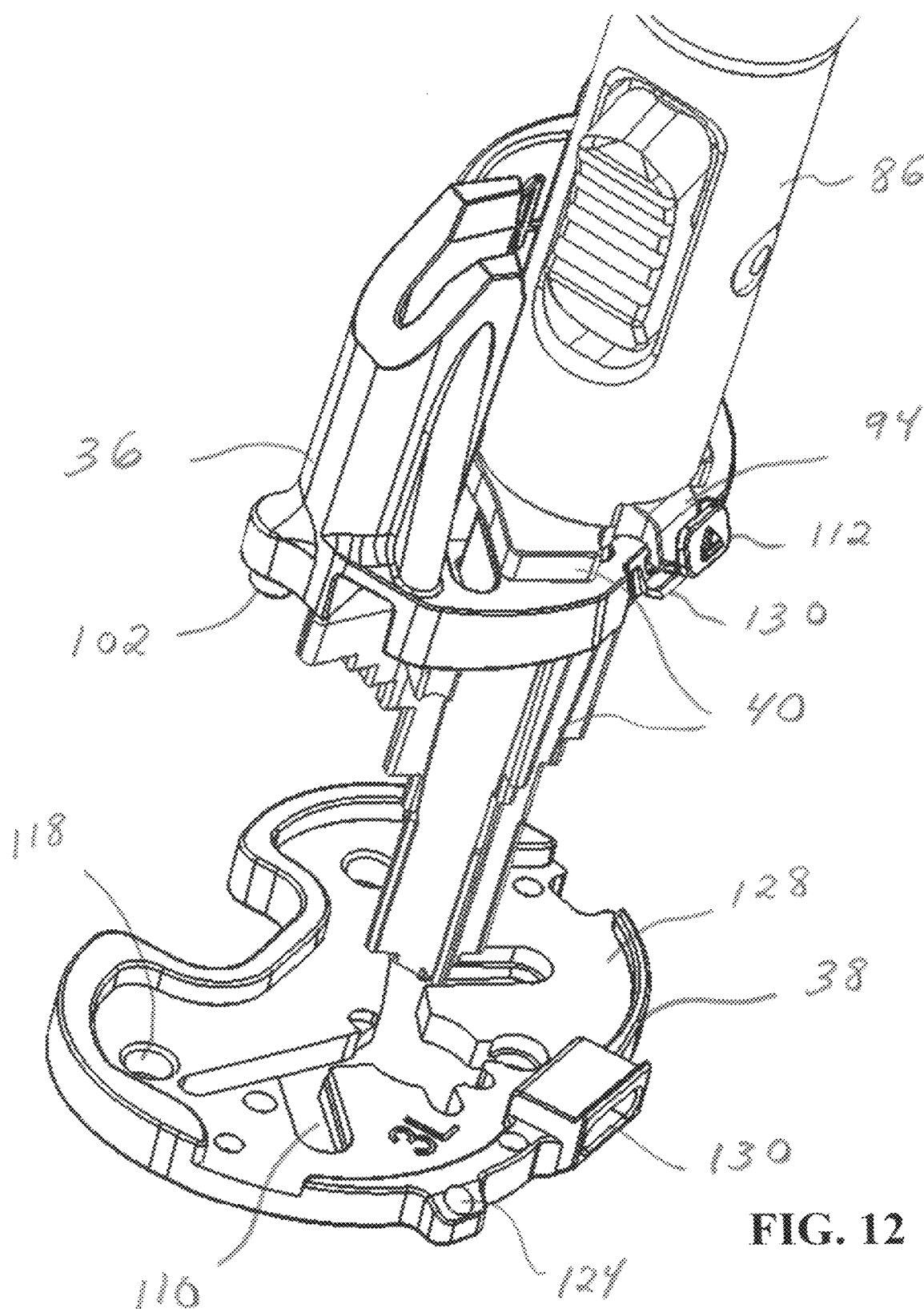
FIG. 12 is perspective view of a handle, a fin punch, and a fin punch guide being removed from a tibia base trial.

At this point in the procedure, the fin punch 40 has been fully driven into the patient's bone and the fin punch 40 has been coupled to the fin punch guide 36 via corresponding connectors 96, 106 as previously described. In addition, the fin punch guide 36 is coupled to the tibia base trial 38 via corresponding connectors 102, 118. Moreover, the lever 120 associated with the tab 112 on the fin punch guide 36 has released the recess surface 134 associated with the trial recess 130 on the tibia base trial 38. Thus, if the coupling force between the fin punch 40 and the fin punch guide 36 is greater than or equal to, depending on the coupling force associated with pinning the tibial base trial 38 to the patient's bone, the coupling force between the fin punch guide 36 and the tibia base trial 38, when a user pulls superiorly on the handle 86, the fin punch guide 36 and the fin punch 40 may be removed from the patient as a single unit while leaving the tibia base trial 38 in place. This is illustrated in FIG. 12, which shows the handle 86, the fin punch 40, and the fin punch guide 36 being removed as a single unit. As previously described, the coupling forces (e.g., the push in and pull-out forces) may be uniquely tailored for each set of components. Advantageously, this allows a surgeon to prepare the knee more efficiently by reducing the number of steps in the procedure.

FIGS. 13A and 13B illustrate the use of the connection mechanisms for connecting various types of trialing devices for knee arthroplasty. As illustrated, in use, the connection mechanisms as described herein can be used to couple, for example, a spacer 60 to a tibia trial insert 136, which, in use, may be used during surgery to evaluate final implant placement and knee kinematics. As illustrated, tabs 16 may protrude from the spacer 60 to mate with a corresponding recess formed in the tibia trial insert 136.

Figure 14A:
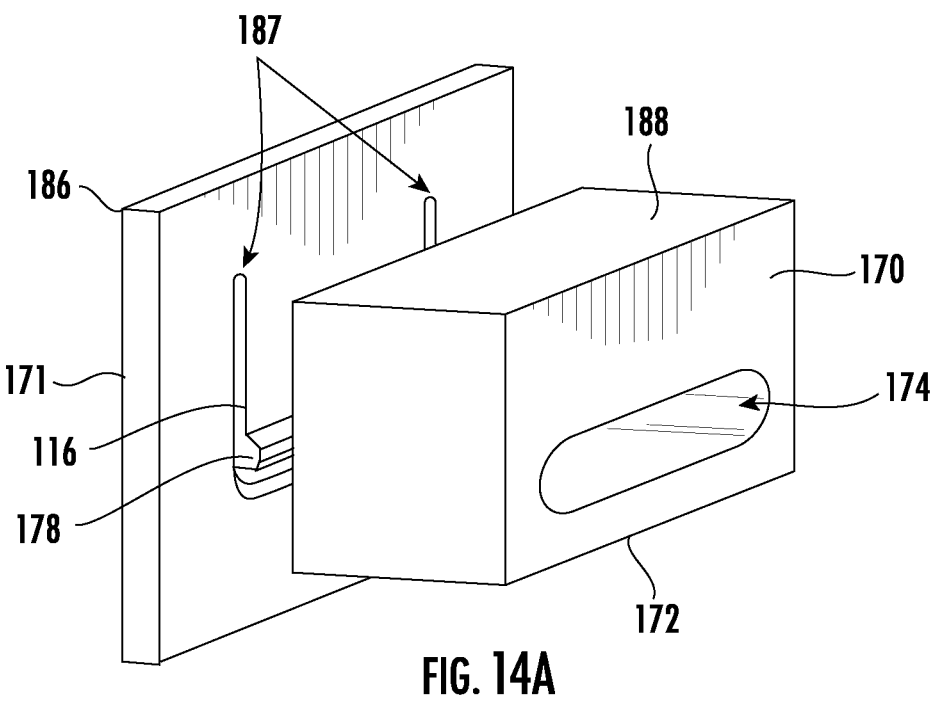
FIGS. 14A and 14B are perspective views of an alternate embodiment of a connection mechanism in accordance with one or more features of the present disclosure.
Figure 14B:
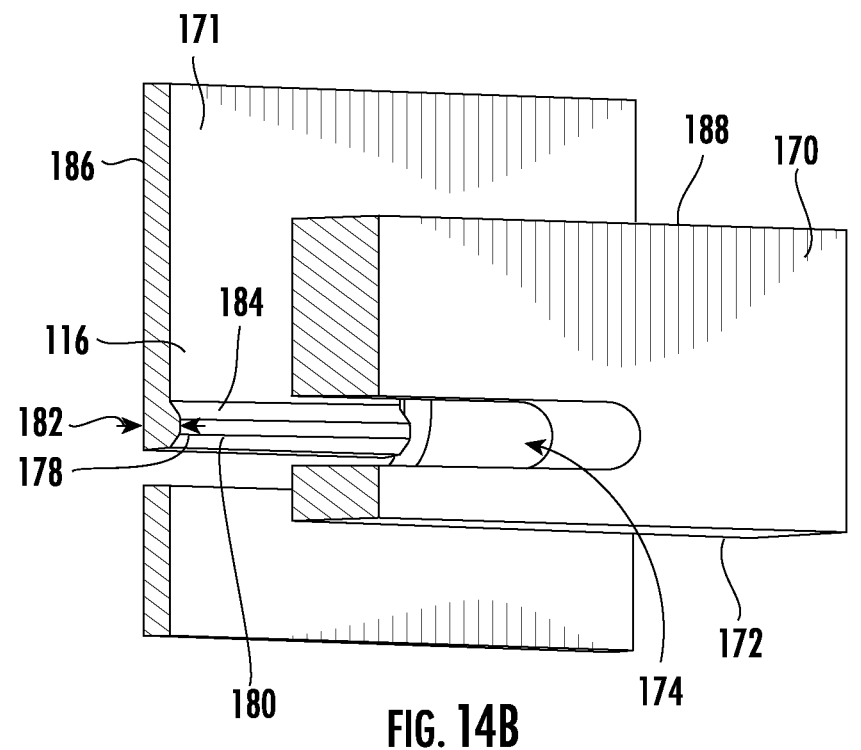

FIGS. 14A-14B illustrate an alternate embodiment of a connection mechanism that may be used to couple first and second components as previously described herein. In this embodiment, the first component 171 includes a surface 186 and a tab 116. In some embodiments, the tab 116 may be formed in the first component 171 by making slits 187 in therein. The tab 116 may include a protrusion 178. The second component 170 includes a surface 172 as well as an opening 174 formed therein and a face 188 opposite the surface 172.

In use, the surface 186 of the first component 171 is typically attached to or integrally connected to a surface of a larger component, such as the first surface 10 formed on the first component 4 described above in connection with FIG. 1. Two or more first components 171 may be connected to, or integrally formed on, the surface of this larger component. Similarly, there may be two or more second components 170 connected via the surface 172 to a surface of a second larger component. In use, the first component 171 and the second component 170 are arranged to mate when the surfaces of the larger components are brought together. As in the previous embodiments, a plurality of first and second components 171, 172 may be provided in any particular configuration (e.g., three first components arranged in a triangle, four first components arranged in a square, with a corresponding number and arrangement of second components.)

As the two larger components (not shown) are brought together, the tab 116 formed on the first component 171 contacts the face 188 formed on the second component 170. In use, the material of the first component 171 should be sufficiently resilient to allow the tab 116 to deflect or bend in response to an applied stress. As the larger components are brought further together and the tab 116 contacts the opening 174 formed in the second component 170, the tab 116 releases to an undeflected or partially deflected state, coupling the first and second components 171, 170 together.

As in the previous embodiments, selection of an appropriate height 182 for the protrusion 178 will alter the push-in and pull-out force. Also as in the previous embodiments, selection of an appropriate angle for the leading edge 180 and trailing edge 184 may alter how quickly the push-in and pull-out forces are ramped up to a maximum.

Figures 15A, 15B:
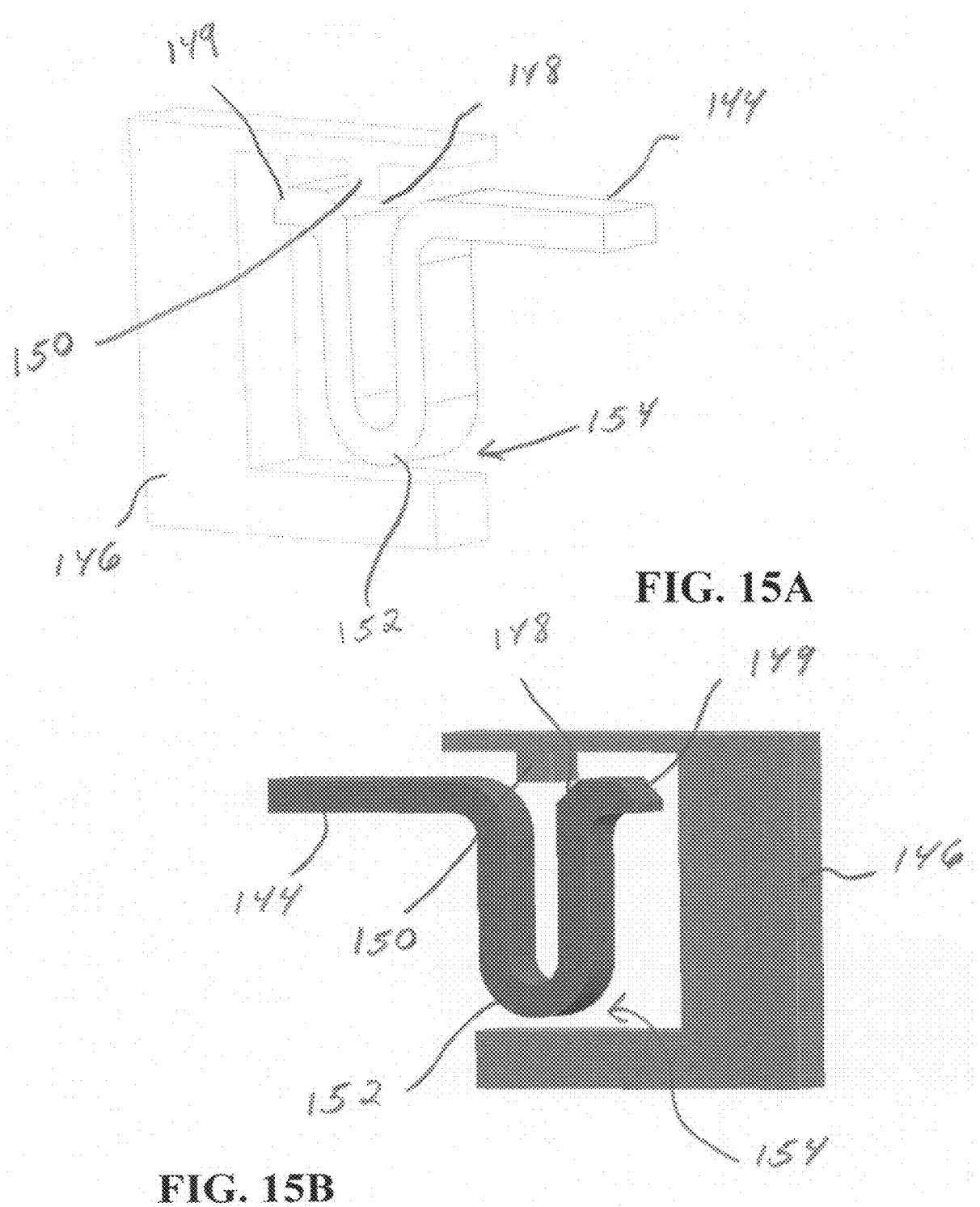
FIGS. 15A-15C are perspective views of an alternate embodiment of a connection mechanism in accordance with one or more features of the present disclosure.
Figure 15C:
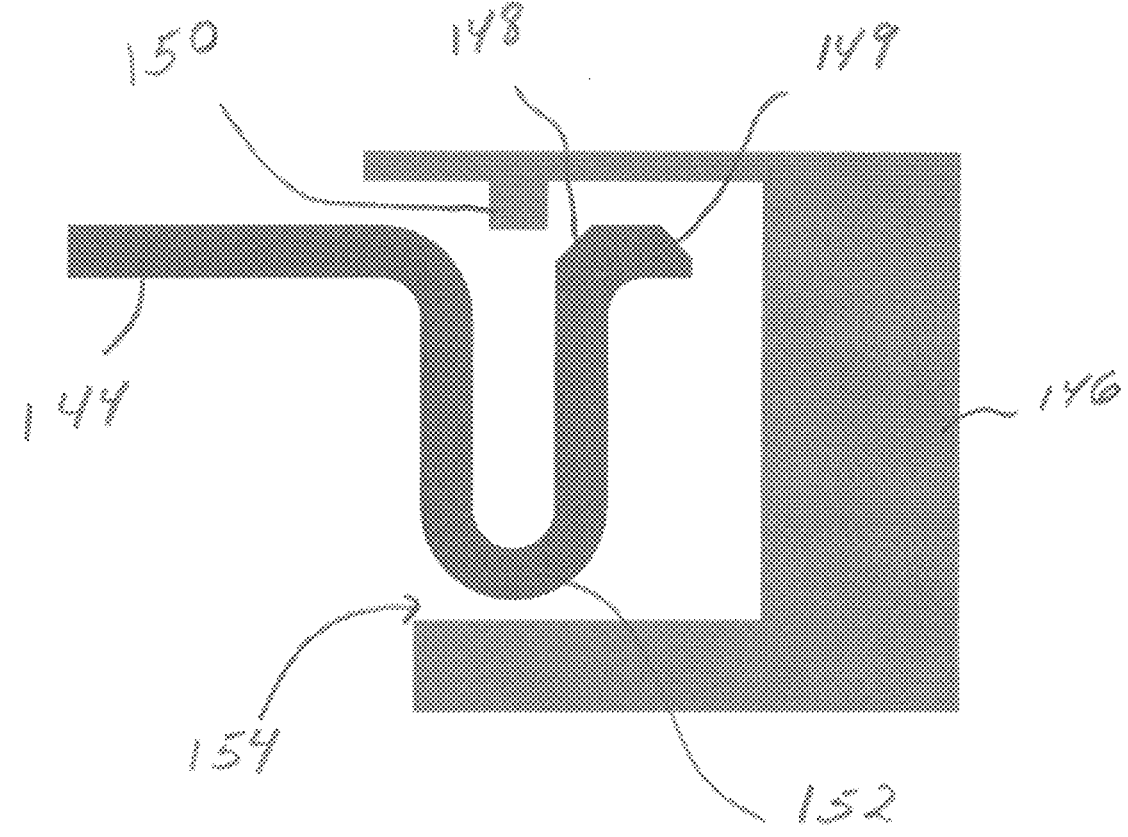

FIGS. 15A-15C illustrate another alternate embodiment of a connection mechanism that may be used to couple first and second components as previously described herein. For simplicity, only the connecting portions are shown, but these parts could be used with any of the specific components of knee instrumentation previously described. In this embodiment, the first component 144 includes a U-bend 152 and a distal chamfer 148. In use, the U-bend 152 allows the first component 144 to deflect as it passes a nub 150 formed on or associated with a second component 146 as the first component 144 is being inserted into the second component 146. Similar to the previous embodiments, tailoring the size of the nub 150, the distal chamfer 148, and the clearance 154 between a surface of the U-bend 152 and the second component allows one to tailor the push-in and pull-out forces of the connection mechanism. In use, the clearance 154 allows for some slop or wiggle in the components when they are connected and increasing the size of the nub 150 increases the amount of push-in and pull-out force needed. The first component 144 and/or the second component 146 may be made of materials having different moduli of elasticity, thus increasing or decreasing the deflection when the first component 144 is inserted. And like the previous embodiments, changing the angle on the proximal chamfer 149, which is arranged and configured to contact the nub 150 during insertion, and/or the distal chamfer 148, which is arranged and configured to contact the nub 150 during removal or decoupling, allows the push-in and pullout force profile to be modified, respectively.

Figure 16A:
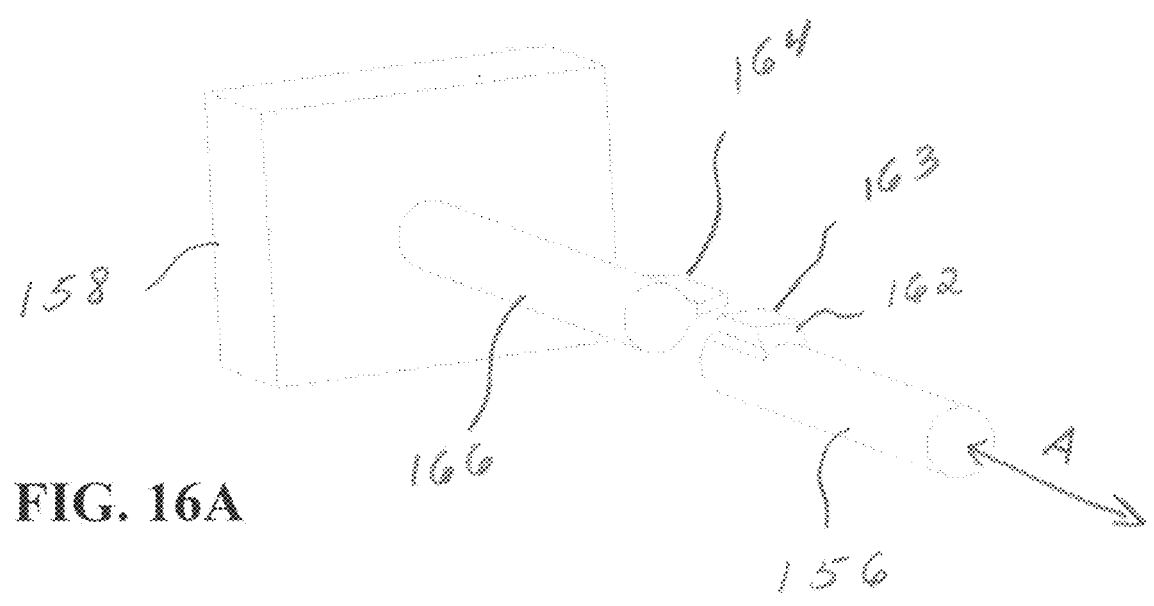
FIGS. 16A and 16B are perspective views of an alternate embodiment of a connection mechanism in accordance with one or more features of the present disclosure.
Figure 16B:
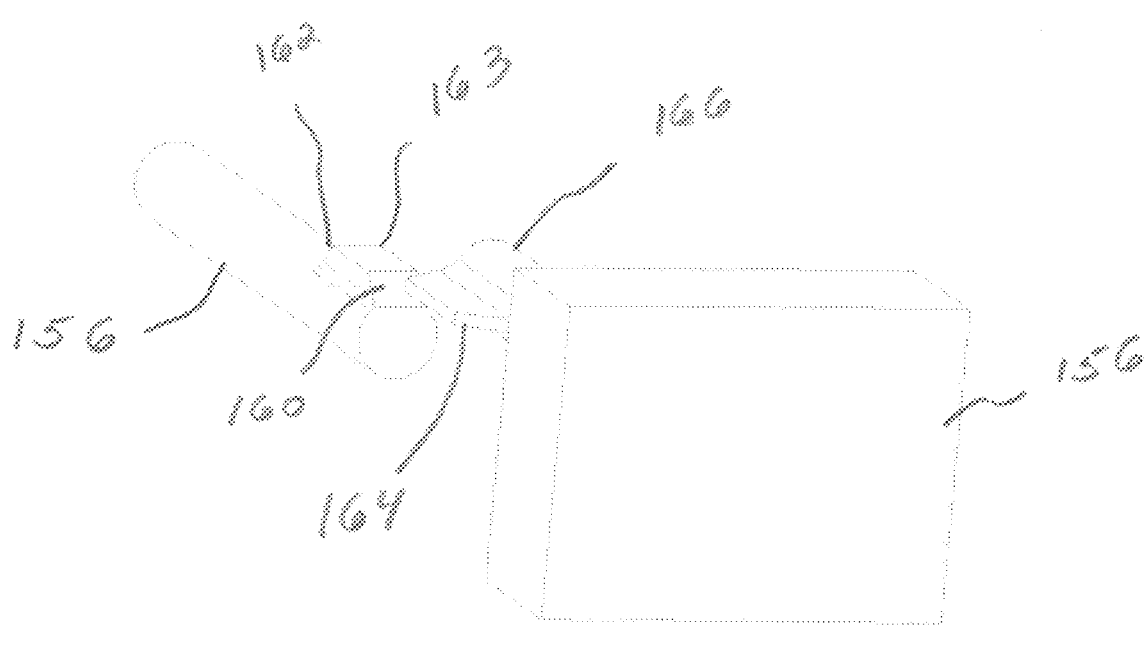

FIGS. 16A-16B illustrate another alternate embodiment of a connection mechanism that may be used to couple first and second components as previously described herein. For simplicity, only the connecting portions are shown, but these parts could be used with any of the specific components of knee instrumentation previously described. In this embodiment, the first component 156 may be connected to the second component 158 by urging the first component 156 along axis A toward the second component 158. In use, the first component 156 includes a prong or nub 163, which is arranged and configured to contact a flange 164, which may be positioned on a rod or shaft 166 extending from the second component 158. During insertion, the prong or nub 163 pushes the flange 164 and the associated rod 166 on the second component 158 causing the flange 164 to rotate under stress about axis A. Once the prong 163 has cleared the flange 164, the rod 166 is free to return to an unstressed state thereby coupling the first and second components. As in the previous embodiments, the height of the prong 163 influences the maximum push-in and pull-out force and the shape of the chamfers 160, 162 associated with the prong 163 allows the push-in and pullout force profile to be modified, respectively. And similar to the previous embodiments, the choice of material for the first component 156 and the second component 158 increases or decreases the deflection of the rod 166.

Figures 17A, 17B:
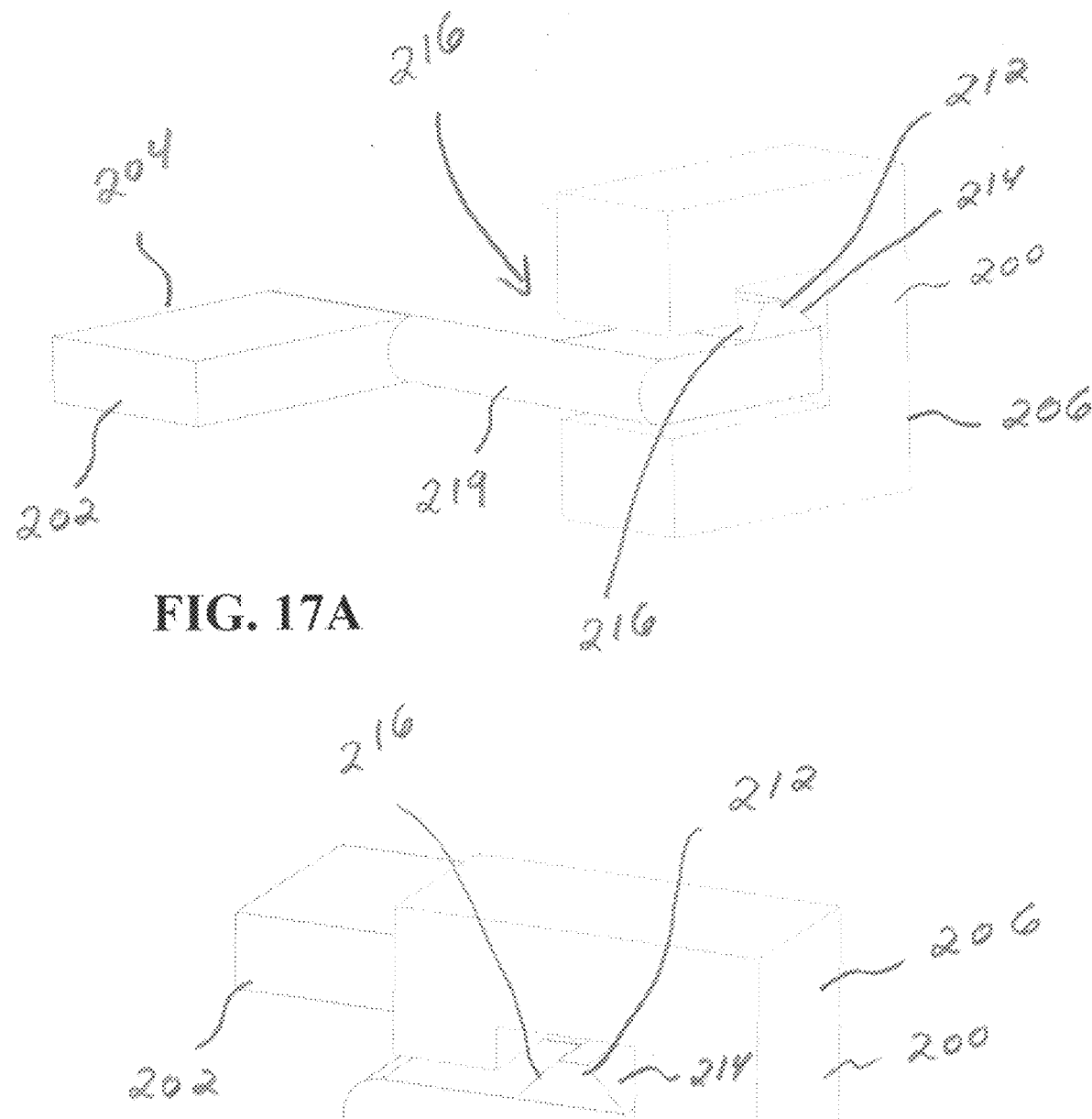
FIGS. 17A and 17B are perspective views of an alternate embodiment of a connection mechanism in accordance with one or more features of the present disclosure.

FIGS. 17A-17B illustrate another alternate embodiment of a connection mechanism that may be used to couple first and second components as previously described herein. In this embodiment, the first component 202 includes a surface 204 and a protrusion 212. The second component 200 includes a surface 206 as well as an opening 216.

In use, the surface 204 of the first component 202 is typically attached to or integrally connected to a surface of a larger component, such as the first surface 10 of the first component 4 from FIG. 1. Two or more first components 202 may be connected to the surface of this larger component. Similarly, there may be two or more second components 200 connected via the surface 206 to a surface of a second larger component. In use, the first component 202 and the second component 200 are arranged to mate when the surfaces of the larger components are brought together. As in the previous embodiments, a plurality of first and second components 202, 200 may be provided in any particular configuration (e.g., three first components arranged in a triangle, four first components arranged in a square, with a corresponding number and arrangement of second components.)

As the two larger components (not shown) are brought together, the protrusion 212 associated with the first component 202 enters the opening 216 formed in the second component 200. The material of the first component 202 should be sufficiently resilient to allow the protrusion 212 to deflect or bend via, for example, an arm 219 in response to an applied stress. As the larger components are brought together, the protrusion 212 passes the nubbins 208 on the second component 200, the protrusion 212 releases to an undeflected or partially deflected state, coupling the first component 202 to the second component 200. As in the previous embodiments, selection of an appropriate height for the protrusion 212 will alter the push-in and pull-out force. Also as in the previous embodiments, selection of an appropriate angle for the leading edge 214 and the trailing edge 216 may alter how quickly the push-in and pull-out forces are ramped up to a maximum.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed in any arthroplasty or other situation where two components need to be releasably connected, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order, and relative sizes reflected in the drawings attached hereto may vary.

We claim:

1. An orthopedic knee system comprising:
   a tibial base trial including an inferior surface arranged and configured to contact a resected tibia, a superior surface opposite the inferior surface, at least one first connector, and a recess including a surface;
   a fin punch guide including an inferior surface arranged and configured to contact the superior surface of the tibial base trial, a superior surface opposite the inferior surface, at least one second connector arranged and configured to couple with the at least one first connector, at least one third connector, and a fin punch guide tab including a lever or hook-shaped end portion configured to reside within the recess and to contact the surface when the fin punch guide is coupled to the tibial base trial; and
   a fin punch including at least one fourth connector arranged and configured to couple with the at least one third connector and a projection or tab configured to contact the fin punch guide tab during connection of the fin punch to the fin punch guide, contact of the projection or tab moving the fin punch guide tab to a second position thereby releasing the lever or hook-shaped end portion from the recess so that removing the fin punch causes the fin punch guide to disconnect from the tibial base trial;
   wherein at least one of the first connector and the second connector includes a male mating feature, and the other one of the first connector and the second connector includes a female mating feature; and wherein at least one of the third connector and the fourth connector includes a male mating feature, and the other one of the third connector and the fourth connector includes a female mating feature.

2. The orthopedic knee system of claim 1, wherein the male mating feature of the first and second connectors includes a plurality of tabs; and the female mating feature of the first and second connectors includes a recess arranged and configured to receive the male mating feature of the first and second connectors.

3. The orthopedic knee system of claim 2, wherein the male mating feature of the first and second connectors further includes a boss, the plurality of tabs circumferentially spaced about the boss.

4. The orthopedic knee system of claim 2, wherein the recess includes a circumferential chamfer arranged and configured to guide insertion of the male mating feature of the first and second connectors; a first section having a first diameter; and a second section having a second diameter, wherein the second diameter is greater than the first diameter.

5. The orthopedic knee system of claim 1, wherein coupling the male mating feature to the female mating feature provides tactical feedback including an audible sound.

6. The orthopedic knee system of claim 1, wherein the tibial base trial includes a first passageway formed therein, the fin punch guide includes a second passageway formed therein, the second passageway aligned with the first passageway when the fin punch guide is coupled to the tibial base trial so that a portion of the fin punch can pass through the fin punch guide, through the tibial base trial and into the resected tibia.

* * * * *